US010850107B2

(12) United States Patent
Li et al.

(10) Patent No.: US 10,850,107 B2
(45) Date of Patent: Dec. 1, 2020

(54) AUTOMATED OPTIMIZATION OF HIS BUNDLE PACING FOR CARDIAC RESYNCHRONIZATION THERAPY

(71) Applicant: PACESETTER, INC., Sytlmar, CA (US)

(72) Inventors: Wenwen Li, San Jose, CA (US); Gene A. Bornzin, Simi Valley, CA (US); Nima Badie, Berkeley, CA (US); Stuart Rosenberg, Woodbury, MN (US); Luke C. McSpadden, Los Angeles, CA (US); Kyungmoo Ryu, Palmdale, CA (US)

(73) Assignee: PACESETTER, INC., Sylmar, CA (US)

( * ) Notice: Subject to any disclaimer, the term of this patent is extended or adjusted under 35 U.S.C. 154(b) by 101 days.

(21) Appl. No.: 16/181,234

(22) Filed: Nov. 5, 2018

(65) Prior Publication Data
US 2020/0139130 A1 May 7, 2020

(51) Int. Cl.
*A61N 1/365* (2006.01)
*A61N 1/02* (2006.01)
(Continued)

(52) U.S. Cl.
CPC ......... *A61N 1/36507* (2013.01); *A61N 1/025* (2013.01); *A61N 1/056* (2013.01);
(Continued)

(58) Field of Classification Search
CPC .... A61N 1/36507; A61N 1/025; A61N 1/056; A61N 1/3627; A61N 1/3684; A61N 1/371
See application file for complete search history.

(56) References Cited

U.S. PATENT DOCUMENTS 6,718,206 B2 4/2004 Casavant
8,565,880 B2 10/2013 Dong et al.
(Continued)

FOREIGN PATENT DOCUMENTS

CN 105148403 B 8/2018

OTHER PUBLICATIONS

International Search Report and Written Opinion for corresponding PCT Application No. PCT/US2019/056171 dated Mar. 26, 2020.

*Primary Examiner* — Tammie K Marlen
(74) *Attorney, Agent, or Firm* — The Small Patent Law Group LLC; Dean D. Small

(57) ABSTRACT

Systems and methods of performing cardio resynchronization therapy (CRT) on a patient heart include the use of a stimulation system having at least one processor, at least one memory, a pulse generator, a stimulating electrode disposed in proximity to a His bundle of the patient heart, and a sensing electrode adapted to sense electrical activity of the left ventricle (LV) of the patient heart. CRT is provided by applying, using the pulse generator and through the stimulating electrode, a His bundle pacing (HBP) impulse having a first impulse energy. The sensing electrode is then used to measure an LV activation time in response to the HBP impulse. At least one setting of the pulse generator is modified based on the LV activation time such that a subsequent HBP impulse may be provided by the pulse generator via the stimulating electrode using a modified impulse energy.

20 Claims, 9 Drawing Sheets

(51) Int. Cl.
*A61N 1/05* (2006.01)
*A61N 1/362* (2006.01)
*A61N 1/368* (2006.01)
*A61N 1/37* (2006.01)

(52) U.S. Cl.
CPC ......... *A61N 1/3627* (2013.01); *A61N 1/3684* (2013.01); *A61N 1/371* (2013.01)

(56) References Cited

U.S. PATENT DOCUMENTS

| | | |
|---|---|---|
| 8,934,969 B2 | 1/2015 | Zhu et al. |
| 9,162,066 B2 | 10/2015 | Hedberg et al. |
| 2008/0269823 A1 | 10/2008 | Burnes et al. |
| 2008/0319501 A1 | 12/2008 | Zhu et al. |
| 2009/0112276 A1 | 4/2009 | Yu et al. |
| 2011/0230922 A1 | 9/2011 | Fishel |
| 2012/0239106 A1 | 9/2012 | Maskara et al. |
| 2014/0005740 A1 | 1/2014 | Ghos et al. |
| 2014/0277237 A1 | 9/2014 | Maskara et al. |
| 2019/0192860 A1* | 6/2019 | Ghosh .................. A61N 1/3706 |
| 2019/0201698 A1* | 7/2019 | Herrmann ............... A61N 1/365 |
| 2020/0009390 A1* | 1/2020 | Casavant ............. A61B 5/0464 |

* cited by examiner

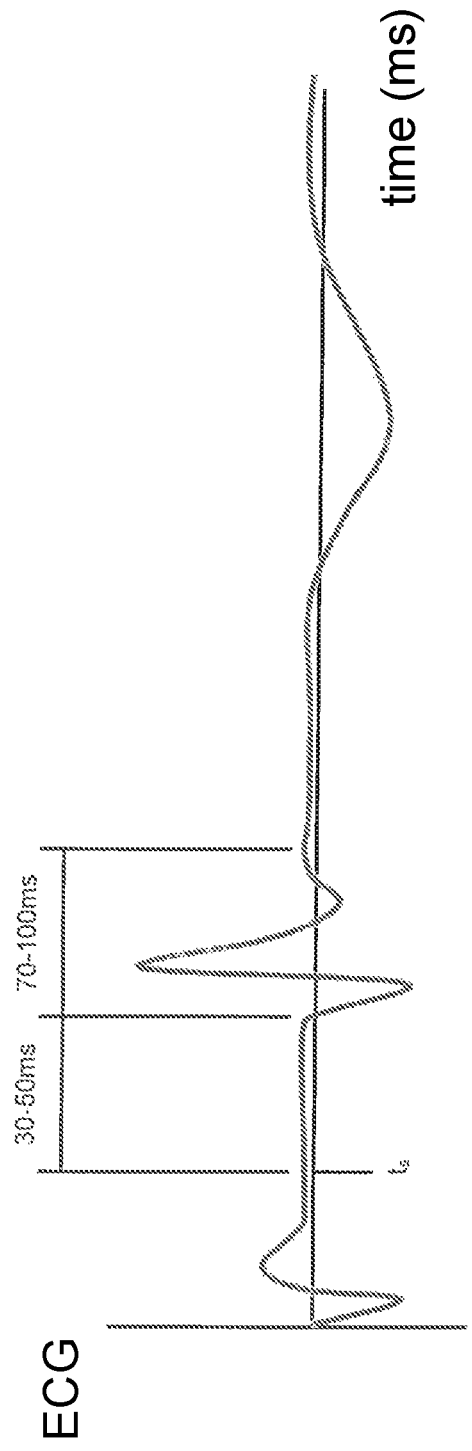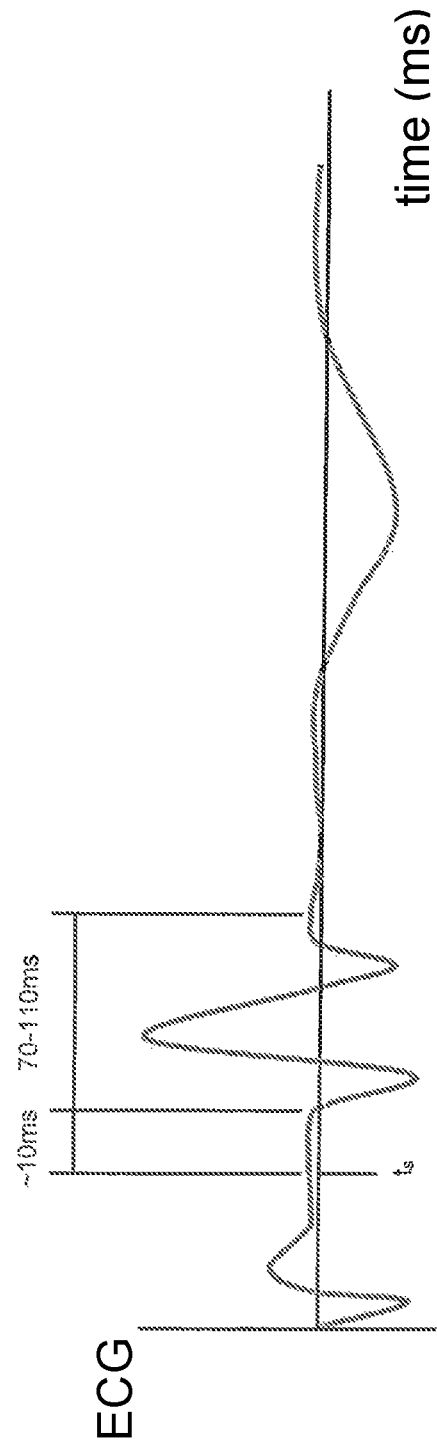

AUTOMATED OPTIMIZATION OF HIS BUNDLE PACING FOR CARDIAC RESYNCHRONIZATION THERAPY

FIELD

This disclosure relates generally to implantable cardiac stimulating devices. More specifically, the present disclosure is directed to a cardiac stimulation system that includes a lead for His bundle pacing and that includes logic for automatically identifying and implementing settings of the cardiac stimulation system for delivering His bundle pacing for purposes of cardiac resynchronization therapy (CRT). This disclosure further relates to a method for performing CRT using such a stimulation system.

BACKGROUND

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (AV) node and a ventricular conduction system comprised of the bundle of His (also referred to as the His bundle), the left and right bundle branches, and the Purkinje fibers, causing a depolarization and the resulting ventricular chamber contractions. The depolarization of the interventricular septum and ventricles is generally referred to as a QRS complex and is observed and measured through the use of electrocardiograms (ECGs) and similar equipment for measuring electrical activity of the heart.

Disruption of this natural pacemaking and conduction system as a result of aging or disease can be successfully treated by artificial cardiac pacing using implantable cardiac stimulation systems, including pacemakers and implantable defibrillators, which deliver rhythmic electrical pulses or other anti-arrhythmia therapies to the heart, via electrodes implanted in contact with the heart tissue, at a desired energy and rate. To the extent the electrical pulses are sufficient to induce depolarization of the associated heart tissue, the heart tissue is said to be captured and the minimum electrical pulse resulting in capture is generally referred to as the capture threshold.

In the majority of individuals, the most effective heartbeat is triggered by the patient's own natural pacing physiology. Implantable cardiac stimulation systems are intended to fill in when the natural pacing functionality of the patient's heart fails or acts inefficiently (such as in cases of sinus arrest and symptomatic bradycardia, respectively) or when the heart's conduction system fails or acts inefficiently (such as in cases of third-degree and second-degree (i.e., Mobitz II) AV blocks, respectively). In a large number of heart failure patients, natural conduction through the AV node and the His bundle are intact and disruption of ventricular rhythm is the result of conduction disorders residing in the left and/or right bundle branches.

Dilatation of the heart due to congestive heart failure (CHF) has been associated with delayed conduction through the ventricles. This delayed conduction leads to reduced hemodynamic efficiency of the failing heart because of the resulting poor synchronization of the heart chambers.

Direct stimulation of the His bundle (i.e., His bundle pacing (HBP)) has been found to provide hemodynamic improvement for various patients including those suffering from dilated cardiomyopathy but having normal ventricular activation. Other examples of patients that may benefit from direct stimulation of the His bundle include those with atrioventricular junction (AVJ) ablation or third-degree AV block that require permanent ventricular pacing. Accordingly, the natural conduction system, when intact, can provide hemodynamicaliy optimal depolarization timing of the heart chambers.

Cardiac resynchronization therapy (CRT), a therapy in which electrical impulses are used to synchronize contraction of the ventricles, has been shown to improve cardiac function, longevity, and cardiac remodeling in many patients. However, there is still a relatively low responder rate across patients. To improve results with CRT multipoint pacing for CRT was developed. Such multipoint pacing has been shown to improve responder rate from approximately 70% to as high as 90%. However, a significant portion of patients remain non-responsive who are not responding to CRT or minimally respond to CRT.

As previously noted, HBP has been shown to provide physiologically improved ventricular stimulation, and to promote atrioventricular and interventricular synchrony through intrinsic conduction pathways. Moreover, HBP has also been shown to eliminate various negative effects of long-term right ventricle apical pacing and to correct left bundle branch block (LBBB). Clinical studies further demonstrated that HBP significantly narrows QRS duration, resulting in electrical activity that more closely resembles the natural functioning of the heart. Accordingly, HBP may prove particularly effective in implementing CRT and, in particular, to improve the overall responder rate of patients undergoing CRT.

In light of the foregoing, there is a need for a cardiac stimulation system and associated methods for providing CRT through HBP. To avoid the need for substantial intervention by medical professionals, there is also a need for such a system to operate In a substantially automatic/autonomous, thereby minimizing the amount of intervention required by medical professionals and dynamically adjusting settings of the system in response to changes in a patient's physiology and condition.

BRIEF SUMMARY OF THE DISCLOSURE

In one aspect of the present disclosure, a method of performing cardio resynchronization therapy (CRT) on a patient heart is provided. Such methods may be performed using a stimulation system having at least one processor, at least one memory, a pulse generator, a stimulating electrode disposed in proximity to a His bundle of the patient heart, and a sensing electrode adapted to sense electrical activity of the left ventricle (LV) of the patient heart. The method includes applying, using the pulse generator and through the stimulating electrode, a His bundle pacing (HBP) impulse having a first impulse energy and measuring, using the sensing electrode, an LV activation time in response to the HBP impulse. The method further includes modifying, based on the LV activation time, at least one setting of the pulse generator stored in the at least one memory such that a subsequent HBP impulse to be provided by the pulse generator via the stimulating electrode has a second impulse energy different from the first impulse energy. In certain implementations, the at least one setting of the pulse generator includes at least one of an HBP impulse amplitude and an HBP impulse duration.

In one implementation, the stimulation system further includes a second sensing electrode adapted to sense electrical activity of the His bundle. In such implementations, the method further includes identifying an atrial event, the atrial event being one of a pacing of the right atrium (RA) and a sensing of intrinsic RA activation and identifying, using the second sensing electrode, an intrinsic His bundle activation corresponding to the atrial event. The system then determines a His bundle activation time, which is a time between the atrial event and the intrinsic His bundle activation, and sets an HBP impulse timing of the pulse generator to be less than the His bundle activation time. By doing so, HBP impulses applied using the stimulating electrode preempt intrinsic His bundle activation. Such implementations may further include collecting dynamic impedance data corresponding to one or more cardiac functions in response to HBP impulses applied by the pulse generator. Based on the dynamic impedance data, the HBP impulse timing may be modified to maximize dynamic impedance.

In another implementation, the method may further include applying, using the pulse generator, an LV impulse to the LV after an LV pacing delay ($t_{HP-LVP}$), $t_{HP-LVP}$ corresponding to a time from application of the HBP impulse. In such implementations, $t_{HP-LVP}$ may be selected to result in a minimal QRS duration. To do so, the method may include applying a plurality of LV timing impulses, each of the plurality of LV timing impulses being applied using a different LV pacing delay. For each LV timing impulse of the plurality of LV timing impulses, a QRS waveform generated in response to application of the LV timing impulse may be measured. For each measured QRS waveform, a respective QRS duration may then be determined and the shortest QRS duration of the respective QRS durations may be identified. A $t_{HP-LVP}$ setting of the pulse generator may then be modified such that $t_{HP-LVP}$ equals that of the LV timing impulse having the shortest QRS duration.

In another implementation, $t_{HP-LVP}$ is based on each of a first intrinsic delay ($t_{HP-RVS}$) between HBP and a response of a right ventricle (RV) of the patient heart, a second intrinsic delay ($t_{HP-LVS}$) between HBP and a response of the LV, and a third intrinsic delay ($t_{LVP-RVS}$) between pacing of the LV and a response of the RV. In such implementations, the method may further include performing HBP by applying a first impulse to the His bundle, measuring each of $t_{HP-LVS}$ and $t_{HP-RVS}$ in response to applying the first impulse, applying a second impulse to the LV, and measuring $t_{LVP-RVS}$ in response to applying the second impulse. Such implementations may also include determining $t_{HP-LVS}$ is less than $t_{HP-RVS}$ and setting $t_{HP-LVP}$ to the lesser of $t_{LVP-RVS}$ and $0.5*(t_{LVP-RVS}+(t_{HP-LVS}-t_{HP-RVS}))$. The method may further include determining $t_{HP-LVS}$ is one of greater than or equal to $t_{HP-RVS}$ and setting $t_{HP-LVP}$ equal to $0.5*(t_{LVP-RVS})$.

In certain implementations, the stimulation system includes a multipolar LV lead including a plurality of LV sensing electrodes. In such implementations, the method may further include measuring a plurality of LV activation delays, each of the plurality of LV activation delay measured using a respective LV sensing electrode of the plurality of LV sensing electrodes. A total LV activation time may then be calculated by subtracting a minimum LV activation delay of the plurality of LV activation delays from a maximum LV activation delay of the plurality of LV activation delays. If the total LV activation time is below a total LV activation time threshold, at least one second LV impulse may be applied to the LV. In such implementations, the total LV activation time threshold may be equal to one half of the minimum LV activation delay.

In another aspect of the present disclosure, a cardiac stimulation system adapted to provide CRT for a patient heart is provided. The stimulation system includes a pulse generator, a stimulating electrode coupled to the pulse generator and configured to be disposed in proximity to a His bundle of the patient heart, a sensing electrode coupled to the pulse generator and adapted to sense electrical activity of an LV of the patient heart, a processor communicatively coupled to the pulse generator, and a memory communicatively coupled to the processor, the memory including instructions executable by the processor. When executed by the processor, the instructions cause the processor to apply, using the pulse generator and through the stimulating electrode, a His bundle pacing (HBP) impulse having a first impulse energy and measure, using the sensing electrode, an LV activation lime in response to the HBP impulse. The instructions further cause the processor to modify, based on the LV activation time, at least one setting of the pulse generator stored in the at least one memory such that a subsequent HBP impulse to be provided by the pulse generator via the stimulating electrode has a second impulse energy different from the first impulse energy.

In one implementation, the cardiac stimulation system further includes a second sensing electrode communicatively coupled to the processor and adapted to sense electrical activity of the His bundle. In such implementations, the instructions may further cause the processor to identify an atrial event, the atrial event being one of a pacing of the right atrium (RA) and a sensing of intrinsic RA activation and to identify, using the second sensing electrode, an intrinsic His bundle activation corresponding to the atrial event. The instructions may further cause the processor to determine a His bundle activation time, the His bundle activation time being a time between the atrial event and the intrinsic His bundle activation, and to set an HBP impulse timing of the pulse generator to be less than the His bundle activation time. By doing so, HBP impulses applied using the stimulating electrode preempt intrinsic His bundle activation.

In certain implementations, the instructions may further cause the processor to measure at least one hemodynamic response of the patient heart in response to application of HBP impulses and to adjust an HBP impulse timing setting of the pulse generator to maximize a hemodynamic response corresponding to a subsequently applied impulse.

The stimulation system may further include a left ventricle (LV) coupled to the pulse generator and adapted to provide an LV impulse to the LV after an LV pacing delay ($t_{HP-LVP}$), $t_{HP-LVP}$ corresponding to a time from application of the HBP Impulse. In such implementations, the instructions may further cause the processor to apply a plurality of LV timing impulses, each of the plurality of LV timing impulses being applied using a respective LV pacing delay. For each LV timing impulse of the plurality of LV timing impulses, the processor may measure a QRS waveform generated in response to application of the LV timing impulse and, for each QRS waveform, determine a respective QRS duration. The processor may further identify a shortest QRS duration of the respective QRS durations and modify an LV pacing delay setting of the pulse generator such that $t_{HP-LVP}$ equals the respective LV pacing delay of the LV timing impulse having the shortest QRS duration.

In still another implementations, the instructions further cause the processor to measure each of a first intrinsic delay ($t_{HP-RVS}$) between HBP and a response of a right ventricle (RV) of the patient heart, a second intrinsic delay ($t_{HP-LVS}$) between HBP and a response of the LV, and a third intrinsic delay ($t_{HP-RVS}$) between pacing of the LV and a response of the RV. The processor may further set $t_{HP-LVP}$ based on each of $t_{HP-VSR}$, $t_{HP-LVS}$, and $t_{LVP-RVS}$.

BRIEF DESCRIPTION OF THE DRAWINGS

The various features of the present disclosure and the manner of attaining them will be described in greater detail with reference to the following description, claims, and drawings, wherein reference numerals are reused, where appropriate, to indicate a correspondence between the referenced items, and wherein:

FIGS. 1A and 1B are example electrocardiograms illustrating selective and non-selective His bundle capture, respectively;

DETAILED DESCRIPTION

Figure 2:
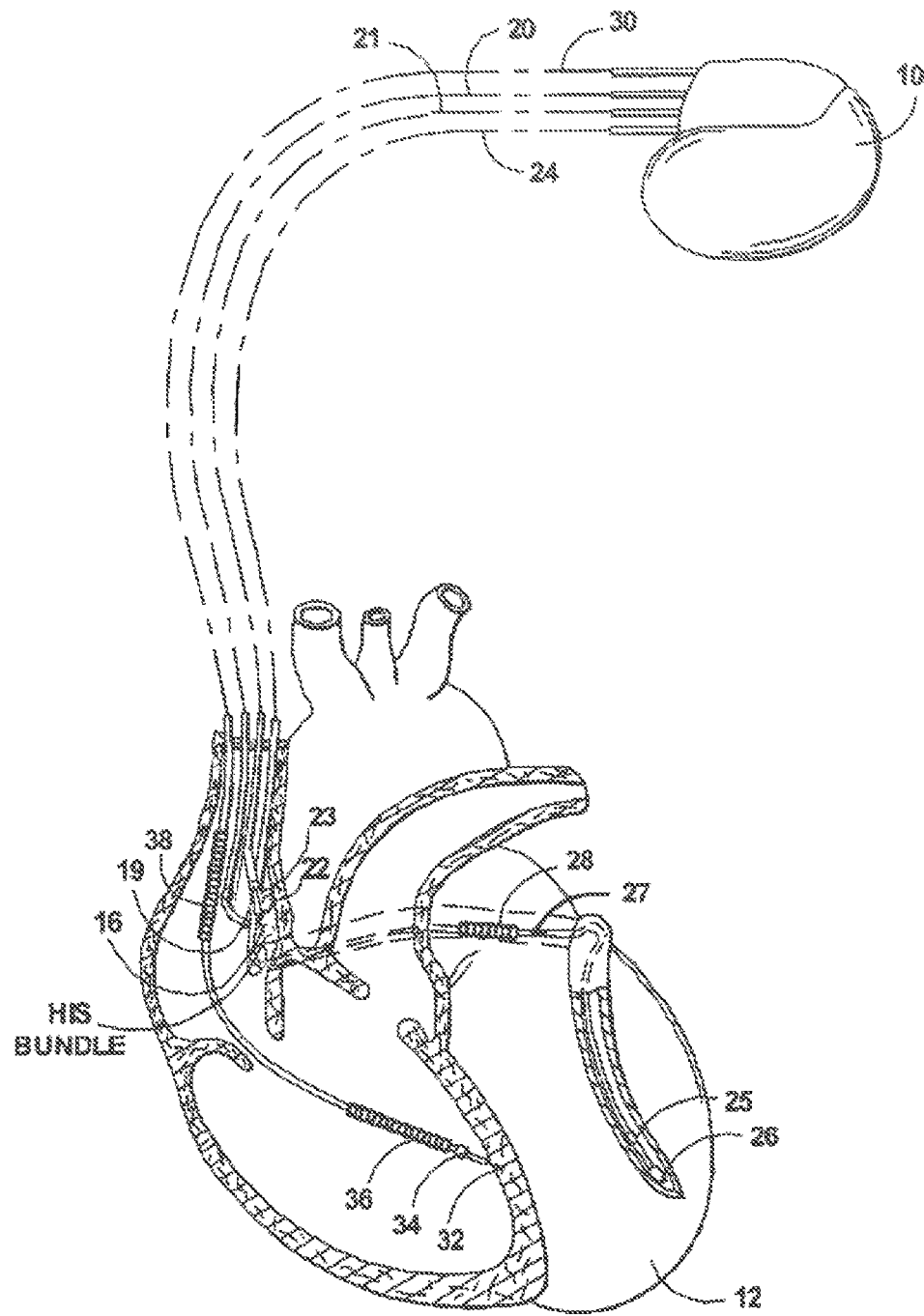
FIG. 2 is a simplified, partly cutaway view illustrating an implantable stimulation system in electrical communication with at least four leads, including a His Bundle lead, implanted into a patient's heart for delivering multi-chamber stimulation and shock therapy.

The present disclosure is directed to systems and methods for performing cardiac resynchronization therapy or CRT. Such systems and methods are directed to providing CRT using His bundle pacing (HBP) and, more specifically, for automatically determining pacing settings (such as impulse energy and timing) to optimize operation of a system for providing CRT using HBP.

Certain cardiac pacemakers and defibrillators incorporate a pacing lead in the right ventricle and may also include a second lead in the fight atrium. High-burden right ventricle pacing may contribute to the development of pacing-induced cardiomyopathy and symptoms associated with heart failure (HF). Several pathophysiologic mechanisms have been implicated in the development of pacing-induced HF, each of which likely stems from non-physiological electrical and mechanical activation patterns produced by right ventricle pacing. His bundle pacing (HBP) may restore physiological activation patterns by utilizing a patient's intrinsic conduction system and may do so even in the presence of bundle branch block. HBP has also been shown to provide significant QRS narrowing, with improved ejection fraction.

Another possible clinical application of HBP is cardiac resynchronization therapy (CRT). Conventional CRT systems include pacing from both a right ventricular and a left ventricular lead, and have been shown most effective for patients exhibiting a wide QRS complex and left bundle branch block. HBP has also been shown to be effective at narrowing the QRS complex in patients with left bundle branch block, likely due to the anatomy of the His bundle, which includes right and left bundle fibers that are longitudinally dissociated. Therefore, what is thought of as left bundle branch block, can be a result of a proximal blockage within the His bundle that eventually branches to the left bundle. As a result, by pacing the His bundle distal to the blockage, a normalized QRS complex can be achieved in some patients. Theoretically, this pacing mode may provide even better results than known CRT treatments, as activation propagates rapidly through natural conduction pathways.

The His bundle is a narrow cluster of cardiac muscle fibers that passes electrical impulses from the AV node to the interventricular septum. It is anatomically located adjacent to the annulus of the tricuspid valve, inferior to or within the membranous septum. During normal functioning of the heart, the delay between excitation of the His bundle and a subsequent depolarization of the ventricles in response to the excitation is generally on the order of approximately 30-50 milliseconds (ms) and the resulting QRS complex generally has a duration of approximately 70-100 ms.

Depending on electrode position, pacing leads targeted for the His bundle may achieve either non-selective or selective HBP. Non-selective His bundle pacing (nsHBP) refers to pacing of the His bundle in which both the His bundle and the local myocardium surrounding the His bundle are captured. Capture occurs when an electrical stimulus applied to the heart is of sufficient energy to depolarize the cardiac tissue, thereby causing the heart muscle to contract. As a result of the simultaneous depolarization of multiple areas of cardiac tissue, the sequential electrical responses typically observed during normal heart activity may be combined or condensed. His bundle capture resulting in such a response is often characterized by the stimulus to ventricular depolarization duration being short, on the order of 20 ms, because the myocardial depolarization propagates immediately without exclusively traveling through the His-Purkinje system. Because the His bundle is stimulated, the QRS duration is similar to the native QRS duration but may be slightly longer due to the myocardial excitation (e.g., 70-120 ms). In contrast, selective His bundle pacing (sHBP) refers to exclusive capture of the His bundle without stimulating surrounding myocardial tissue. With sHBP, the stimulus to ventricular depolarization interval is virtually the same as the native delay between His bundle stimulation and subsequent ventricular depolarization and the QRS duration is essentially identical to the native QRS duration.

To further illustrate the foregoing, FIGS. 1A and 1B are example electrocardiograms corresponding to selective and non-selective His bundle capture, respectively. In each of FIGS. 1A and 1B, a stimulus is applied at a predetermined time ($t_s$) following an atrial event. In FIG. 1A, selective His bundle capture occurs, i.e., only the His bundle is captured and the myocardium is not excited by the stimulus applied at $t_s$. As a result, the delay between application of the stimulus and initiation of the QRS complex is generally in the range of approximately 30 to 50 ms, which is generally consistent with normal heart function. The resulting QRS may be narrowed, but is typically between 70 and 100 ms in duration. The example electrocardiogram of FIG. 1B, in contrast, illustrates non-selective His bundle capture in which the stimulus applied at $t_s$ results in simultaneous capture of both the His bundle and the myocardium. With non-selective capture the delay between application of the stimulus and the initiation of the QRS complex is reduced (typically less than 10 ms) and the QRS duration generally remains between 70 and 120 ms.

Because sHBP more closely approximates native heart function, it is generally preferred to nsHBP. However, due to the complexity and dynamic nature of certain cardiomyopathies and cardiac anatomies, sHBP may not be possible or, if possible at one time, may no longer be possible as a patient's condition changes. Moreover, a patient's condition may also change to the point where HBP is generally unsuitable as a pacing method and ventricular pacing is required.

As previously noted, HBP may be used in the provision of cardiac resynchronization therapy (CRT). CRT improves cardiac function, longevity, and cardiac remodeling in many patients. Nevertheless, recent studies estimate that there is only a 60-70% responder rate in studies related to the effectiveness of conventional CRT techniques. Although the introduction of multipoint pacing for CRT improved responder rates to up to 90%, a significant number of patients do not respond or respond only minimally to CRT.

HBP has been shown to provide physiologically optimal ventricular stimulation, promoting atrioventricular and interventricular synchrony through intrinsic conduction pathways of the heart. HBP has also been shown to eliminate the negative effects of long-term right ventricle (RV) apical pacing. More importantly, HBP has been shown in certain clinical studies to correct left bundle branch block (LBBB) and to significantly narrow QRS duration.

Many physicians are considering using HBP when encountering unsuccessful CRT implant procedures and non-responsiveness to CRT. Currently, there are also ongoing randomized clinical studies to compare outcomes of traditional CRT and HBP as first-line therapies for heart failure patients. Nevertheless, features in CRT devices that allow automatic HBP programming and optimization do not exist.

The present disclosure provides systems and methods that can be readily implemented in CRT devices to automatically program and optimize use of such devices for HBP, thereby benefiting patients requiring CRT. For example, the proposed systems and methods may be implemented to optimize timing and pacing output of CRT devices for CRT patients that are being switched to HBP. By doing so, the overall responder rate for CRT patients, including those patients being upgraded to an HBP-based approach, may be improved.

Figure 6:
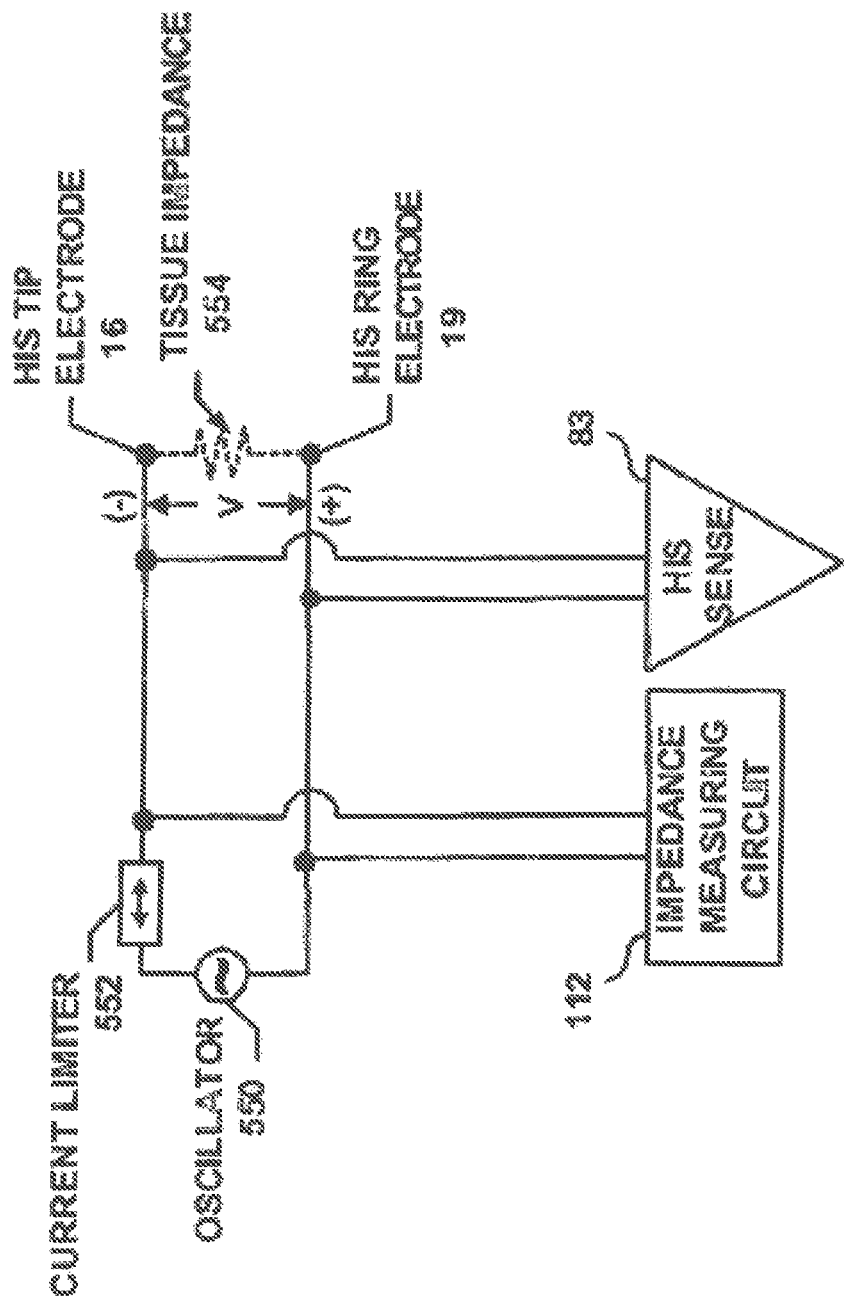
FIG. 6 is an equivalent circuit diagram illustrating a tissue impedance measurement method using the lead of FIG. 4 and the stimulation system of FIG. 3 for locating the His Bundle.
Figure 7:
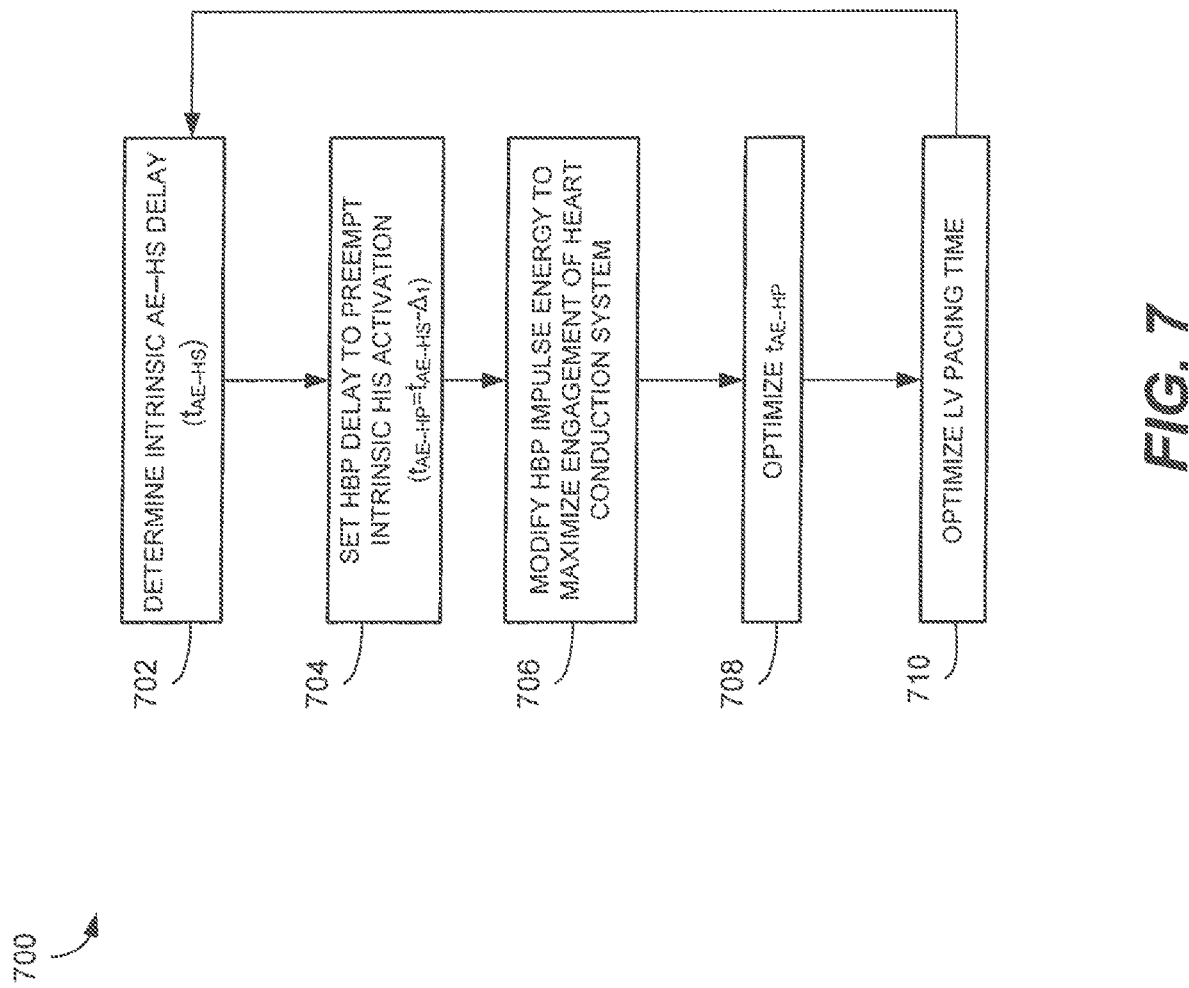
FIG. 7 is a flow chart illustrating a method of automatic programming and optimization of a stimulation system in order to provide cardiac resynchronization therapy (CRT) with His bundle pacing.
Figure 8:
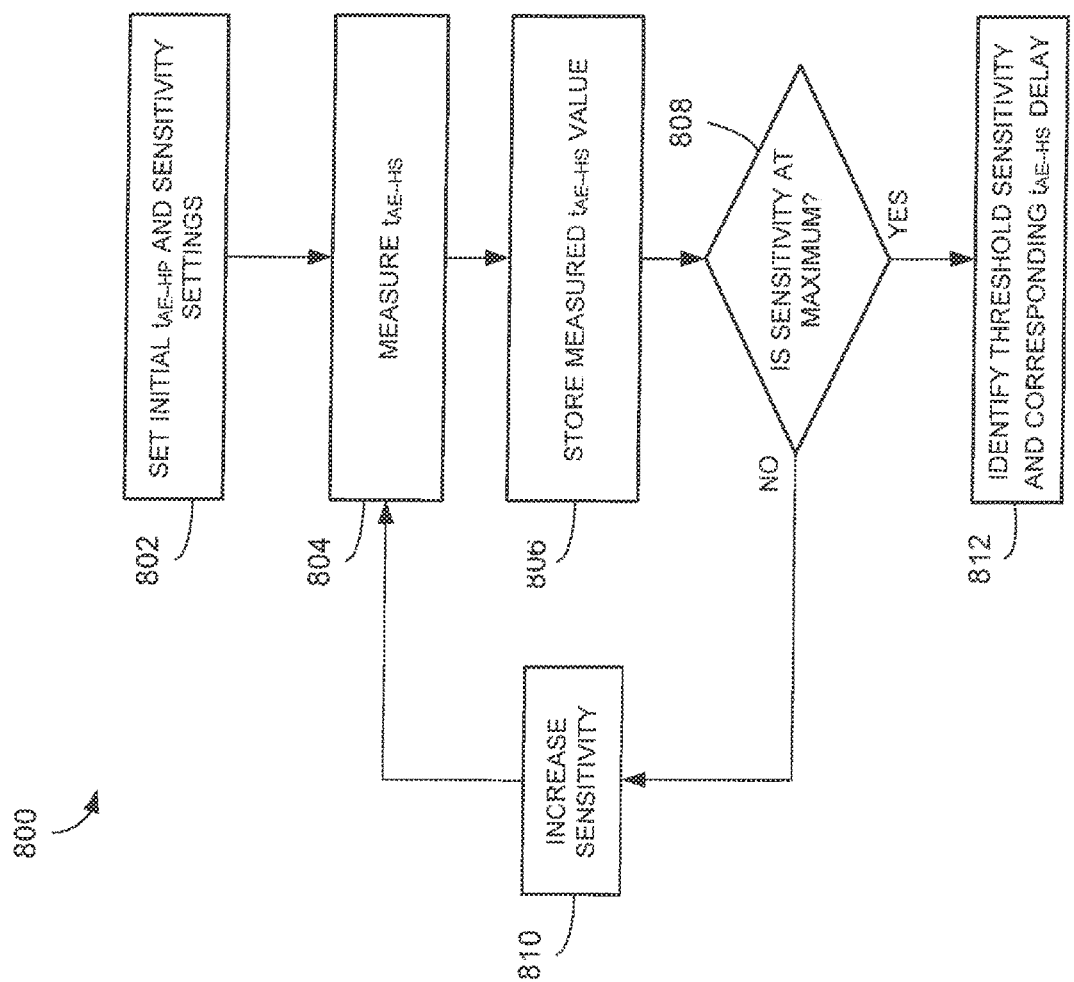
FIG. 8 is a flow chart illustrating an example method of automatically sensing and determining a delay between an atrial event and activation of the His bundle, which may be used In the method of FIG. 7.
Figure 9:
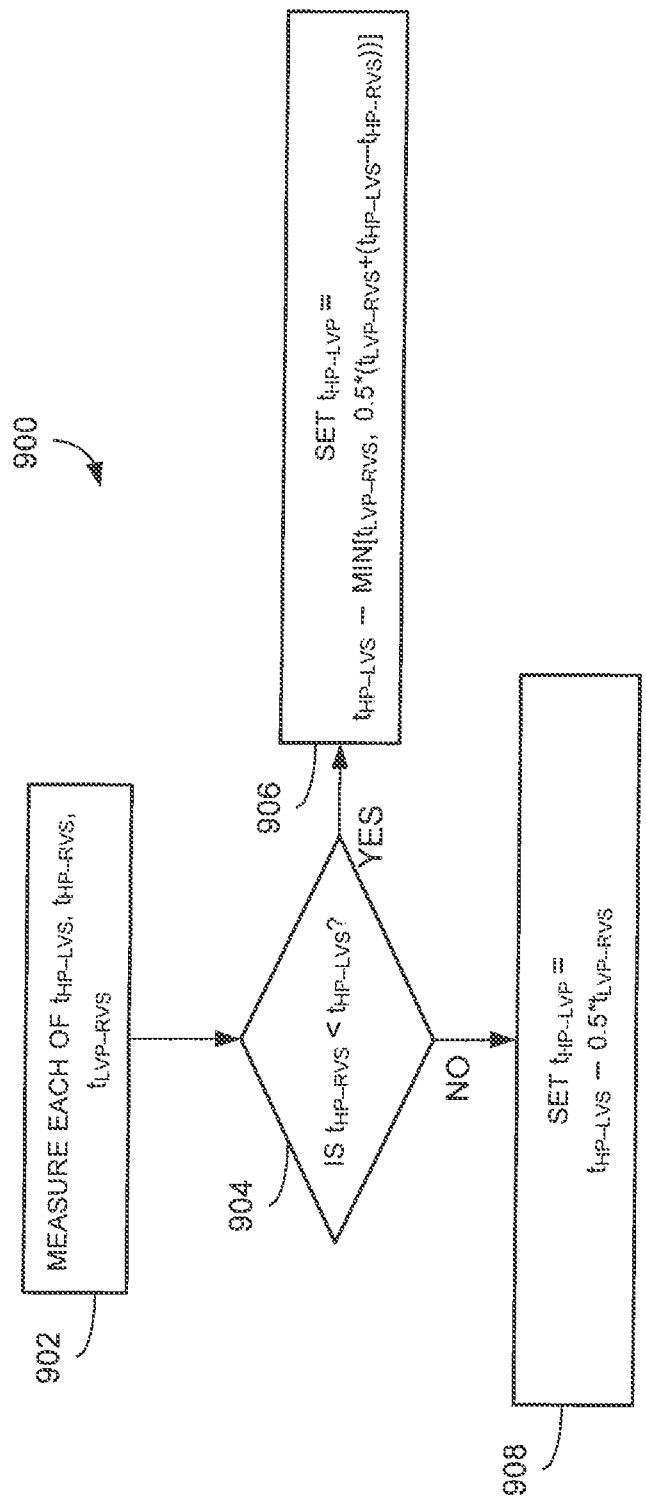
FIG. 9 is a flow chart illustrating an example method of automatically determining a delay between pacing of a His bundle and pacing of a left ventricle of a patient heart, which may be used in the method of FIG. 7.

In light of the foregoing, this disclosure describes methods and apparatuses directed to optimizing HBP for purposes of providing CRT. More specifically, this disclosure describes stimulation systems capable of HBP and processes that may be implemented by such stimulation systems to initialize and dynamically modify settings of the stimulation systems to provide CRT using HBP. To do so, the stimulation systems are generally capable of identifying and dynamically modifying one or more capture thresholds associated with HBP. As discussed below in more details, FIGS. 2-6 generally describe the components and functionality of stimulation systems in accordance with this disclosure while FIGS. 7-9 illustrate various processes that may be implemented by such stimulation systems to provide CRT using HBP.

With reference to FIG. 2, the stimulation system 10 is shown in electrical communication with a patient's heart 12 by way of four leads, 20, 21, 24, and 30 and suitable for delivering multi-chamber stimulation and shock therapy, including CRT. To sense atrial cardiac signals and to provide right atrial chamber stimulation therapy, the stimulation system 10 is coupled to an implantable right atrial lead 20 having at least an atrial tip electrode 22, which typically is implanted in the patient's right atrial appendage or atrial septum.

To sense left atrial and ventricular cardiac signals and to provide left chamber pacing therapy, the stimulation system 10 is coupled to a "coronary sinus" lead 24 designed for placement in the "coronary sinus region" via the coronary sinus ostium for positioning a distal electrode within the coronary veins overlying the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus which overlies the left ventricle.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 26. In another embodiment, an additional electrode for providing left ventricular defibrillation shocking therapy may be included in the portion of the lead overlying the left ventricle, adjacent to the ring electrode 25.

The stimulation system 10 is also shown in electrical communication with the patient's heart 12 by way of an implantable right ventricular lead 30 having, in this embodiment, a right ventricular tip electrode 32, a right ventricular ring electrode 34, a right ventricular coil electrode 36, and a superior vena cava (SVC) coil electrode 38. Typically, the right ventricular lead 30 is transvenously inserted into the heart 12 so as to place the right ventricular tip electrode 32 in the right ventricular apex so that the right ventricular coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

The stimulation system 10 is further connected to a His bundle lead 21 having a His lip electrode 16, such as a helical active fixation device, and a His ring electrode 19 located proximal from the His tip electrode 16. In certain implementations, the His ring electrode 19 is located approximately 10 mm proximal the His tip electrode 16. The His bundle lead 21 may be transvenously inserted into the heart 12 so that the His tip electrode 16 is positioned in the tissue of the His bundle. Accordingly, the His bundle lead 21 is capable of receiving depolarization signals propagated in the His bundle or delivering stimulation to the His bundle, creating a depolarization that can be propagated through the lower conductive pathways of the right and left ventricles (i.e., the right and left bundle branches and Purkinje fibers). The His bundle lead 21 will be described in greater detail in conjunction with FIGS. 5 and 6.

Figure 3:
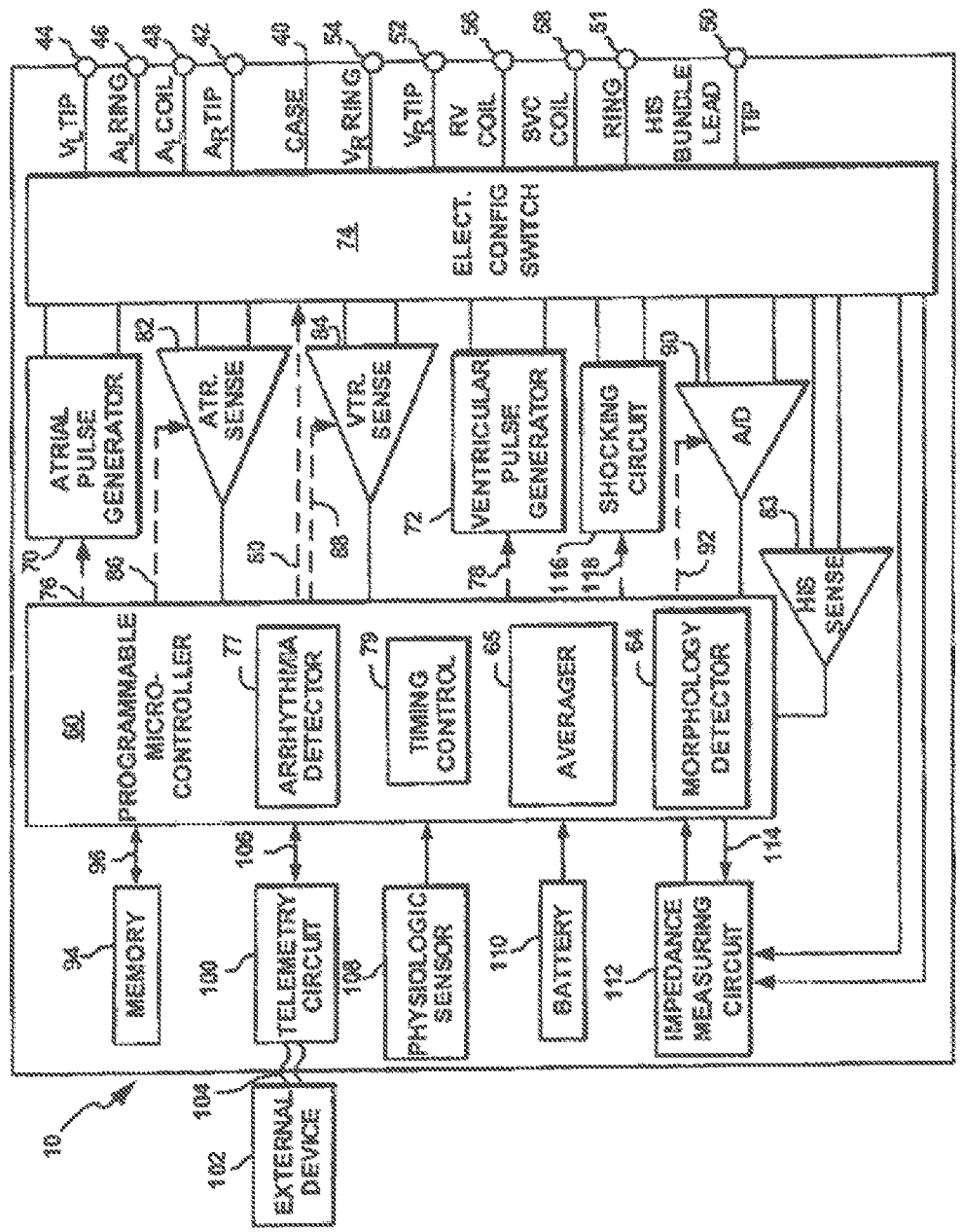
FIG. 3 is a functional block diagram of the multi-chamber implantable stimulation system of FIG. 2, illustrating the basic elements that provide pacing stimulation, cardioversion, and defibrillation in four chambers of the heart.

Referring now to FIG. 3, there is illustrated a simplified block diagram of the multi-chamber implantable stimulation system 10 of FIG. 2, which is capable of treating both fast and slow arrhythmias with stimulation therapy, including cardioversion, defibrillation, and pacing stimulation. The stimulation system 10 may also be used to provide CRT. While a particular multi-chamber device is shown, this is for illustrative purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation system 10, shown schematically in FIG. 3, is often referred to as the "can", "case" or "case electrode" and may be programmably selected to act as the return electrode for all "unipolar" modes. The housing 40 may further be used as a return electrode alone or in combination with one or more of the coil electrodes 28, 36, and 38 (shown in FIG. 2) for shocking purposes. The housing 40 further includes a connector (not shown) having a plurality of terminals 42, 44, 46, 48, 50-52, 54, 56, and 58 (shown schematically and, for convenience, next to the names of the electrodes to which they are connected). As such, to achieve right atrial sensing and pacing the connector includes at least a right atrial tip terminal (A$_R$ TIP) 42 adapted for connection to the atrial tip electrode 22 (shown in FIG. 2).

To achieve left chamber sensing, pacing and shocking, the connector includes at least a left ventricular tip terminal (V$_L$ TIP) 44, a left atrial ring terminal (A$_L$ RING) 46, and a left atrial shocking terminal (A$_L$ COIL) 48, which are adapted for connection to the left ventricular tip electrode 26, the left atrial ring electrode 27, and the left atrial coil electrode 28, respectively (each shown in FIG. 2).

To support right chamber sensing, pacing and shocking, the connector further includes a right ventricular tip terminal (V$_R$ TIP) 52, a right ventricular ring terminal (V$_R$ RING) 54, a right ventricular shocking terminal (RV COIL) 56, and an SVC shocking terminal (SVC COIL) 58, which are adapted for connection to the right ventricular tip electrode 32, right ventricular ring electrode 34, the right ventricular coil electrode 36, and the SVC coil electrode 38, respectively (each shown in FIG. 2).

To achieve His bundle sensing, or sensing and stimulation, the connector further includes a His bundle lead tip terminal 50 and a His bundle lead ring terminal 51 which are adapted for connection to the His tip electrode 16 and the His ring electrode 19, respectively (each shown in FIG. 2).

At the core of the stimulation system 10 is a programmable microcontroller 60 which controls the various modes of stimulation therapy. The microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present disclosure. Rather, any suitable microcontroller 60 may be used that carries out the functions described herein.

As shown in FIG. 3, an atrial pulse generator 70 and a ventricular pulse generator 72 generate pacing stimulation pulses for delivery by the right atrial lead 20, the right ventricular lead 30, the coronary sinus lead 24, and/or the His bundle lead 21 via an electrode configuration switch 74. It is understood that in order to provide stimulation therapy in each of the four chambers of the heart, the atrial and ventricular pulse generators 70, 72 may include dedicated, independent pulse generators, multiplexed pulse generators, or shared pulse generators. The pulse generators 70, 72 are controlled by the microcontroller 60 via appropriate control signals 76, 78, respectively, to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 60 further includes timing control circuitry 79 which is used to control the timing of such stimulation pulses (e.g., pacing rate) as well as to keep track of the timing of refractory periods, blanking intervals, noise detection windows, evoked response windows, alert intervals, marker channel timing, etc., which is well known in the art.

According to one embodiment of the present disclosure, timing control circuitry 79 also controls the onset and duration of a His signal sensing window during which a depolarization signal conducted through the AV node to the His bundle can be detected. Timing control circuitry 79 also controls a timing delay provided alter a detected His signal detection, prior to the delivery of a right and/or left ventricular stimulation pulse.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits 82, 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

According to one embodiment of the present disclosure, a His sensing circuit 83 is selectively coupled to the His bundle lead 21 (shown in FIG. 2) for detecting the presence of a conducted depolarization arising in the atria and conducted to the His bundle via the AV node. As used herein, each of the atrial sensing circuit 82, the ventricular sensing circuit 84, and the His sensing circuit 83, includes a discriminator, which is a circuit that senses and can indicate or discriminate the origin of a cardiac signal in each of the cardiac chambers.

Each sensing circuit 82-84 preferably employs one or more low power, precision amplifiers with programmable gain and/or automatic gain control, bandpass filtering, and a threshold detection circuit to selectively sense the cardiac signal of interest. The automatic gain control enables the device 10 to deal effectively with the difficult problem of sensing the low amplitude signal characteristics of atrial or ventricular fibrillation.

The outputs of the sensing circuits 82-84 are connected to the microcontroller 60 which, in turn, is able to trigger or inhibit the atrial and ventricular pulse generators 70, 72, respectively, in a demand fashion in response to the absence or presence of cardiac activity in the appropriate chambers of the heart.

The atrial and ventricular sensing circuits 82, 84, in turn, receive control signals over signal lines 86, 88, from the microcontroller 60 for purposes of controlling the gain, threshold, polarization charge removal circuitry (not shown), and the timing of any blocking circuitry (not shown) coupled to the inputs of the sensing circuits 82, 84.

For arrhythmia detection, the stimulation system 10 includes an arrhythmia detector 77 that utilizes the atrial and ventricular sensing circuits 82, 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The liming intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90 represented by an A/D converter. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the His bundle lead 21, the coronary sinus lead 24, and the right ventricular lead 30 through the switch 74 to sample cardiac signals across any pair of desired electrodes.

In one embodiment, the data acquisition system 90 is coupled to microcontroller 60, or to other detection circuitry, for detecting a desired feature of the His bundle signal. In one embodiment, an averager 65 is used to determine a sliding average of the His bundle signal during a His signal sensing window using known or available signal averaging techniques.

Advantageously, the data acquisition system 90 may be coupled to the microcontroller 60, or other detection circuitry, for detecting an evoked response from the heart 12 in response to an applied stimulus, thereby aiding in the detection of capture. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed at least once a day during at least the acute phase (e.g., the first 30 days following device implant) and less frequently thereafter. A capture threshold search would begin at a desired starting point (either a high energy level or the level at which capture is currently occurring) and decrease the energy level until capture is lost. The minimum energy at which capture is consistently obtained is known as the capture threshold. Thereafter, a safety margin can be automatically or programmably added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation system 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation system 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, stimulation delays, etc.) at which the atrial and ventricular pulse generators 70, 72 generate stimulation pulses.

A common type of rate responsive sensor is an activity sensor, such as an accelerometer or a piezoelectric crystal, which is mounted within the housing 40 of the stimulation system 10. Other types of physiologic sensors are also known, for example, sensors which sense the oxygen content of blood, respiration rate and/or minute ventilation, pH of blood, ventricular gradient, etc. However, any suitable sensor may be used which is capable of sensing a physiological parameter which corresponds to the exercise stale of the patient. The type of sensor used is not critical to the present disclosure and is shown only for completeness.

The stimulation system 10 additionally includes a battery 110 which provides operating power to all of the circuits shown in FIG. 3. For the stimulation system 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The device 10 is shown in FIG. 3 as having an impedance measuring circuit 112 which is enabled by the microcontroller 60 via a control signal 114. The known uses for an impedance measuring circuit 112 include, but are not limited to, lead impedance surveillance during the acute and chronic phases for detecting proper lead positioning or dislodgement; detecting operable electrodes and conductors; and automatically switching to an operable pair if dislodgement or electrical disruption occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

According to one embodiment of the present disclosure, the His tip electrode 16 and His ring electrode 19 may be selectively coupled via switch 74 to the impedance measuring circuit 112 for performing a tissue impedance measurement. The tissue impedance measurement may be made to determine the location of the His bundle as the His tip electrode 16 or mapping collar 418 as shown in FIG. 4, or sensing electrodes 520-523 (shown in FIG. 5) are advanced along the endocardial surface of the right atrium.

In the case where the stimulation system 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (for example, up to 0.5 joules), moderate (for example, 0.5-10 joules), or high energy (for example, 11-40 joules), as controlled by the microcontroller 60. Such shocking pulses are applied to the patient's heart 12 through at least two shocking electrodes, and as shown in this embodiment, selected from the left atrial coil electrode 28, the right ventricular coil electrode 36, and the SVC coil electrode 38. As noted above, the housing 40 may act as an active electrode in combination with the right ventricular electrode 36, or as part of a split electrical vector using the SVC coil electrode 38 or the left atrial coil electrode 28 (i.e., using the right ventricular electrode 36 as a common electrode).

Cardioversion shocks are generally considered to be of tow to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 4:
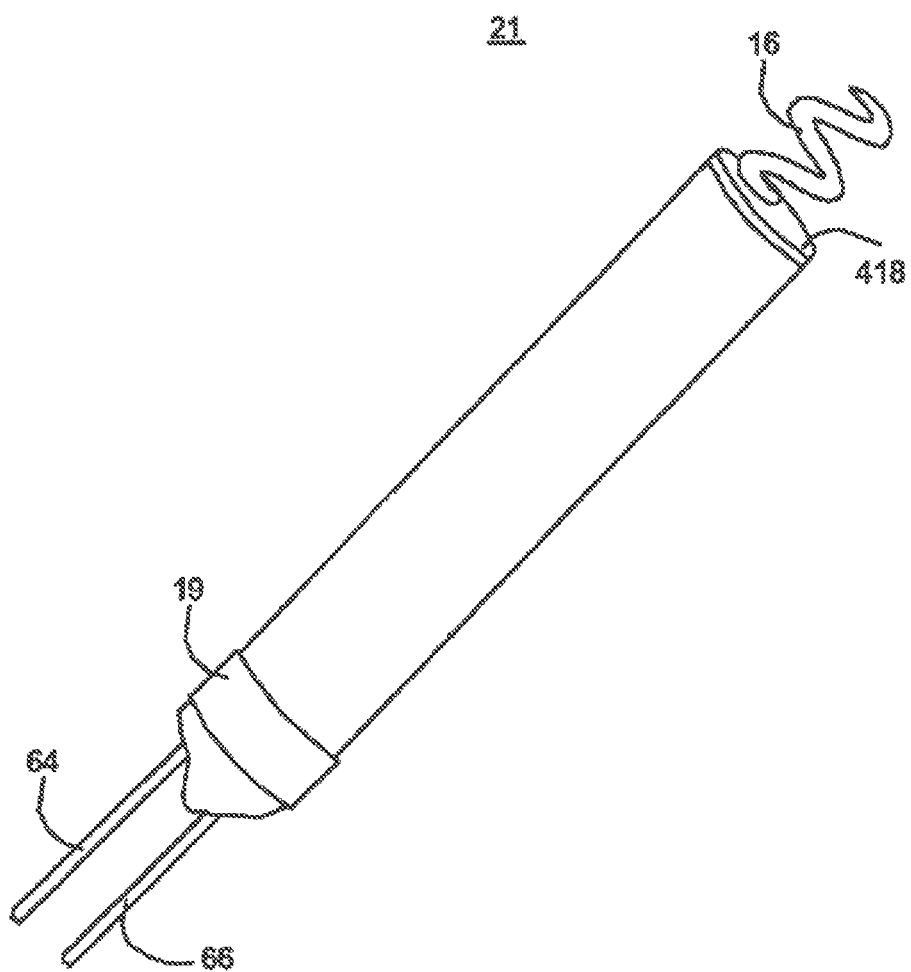
FIG. 4 is a partly fragmentary illustration of the distal end of the His bundle lead for use with the stimulation system of FIG. 3, depicting a tip electrode with an active fixation device and a non-traumatic conductive surface, and a ring electrode.

A more detailed illustration of the His bundle lead 21 is shown in FIG. 4. At the distal end of the lead 21 is the His bundle tip electrode 16. The His bundle tip electrode 16 is, or includes, an active fixation device, such as a helical, "screw-in" device that allows stable fixation of the electrode in the His bundle tissue.

The distal end of the His bundle lead 21 is further provided with a non-traumatic conductive surface (also referred to herein interchangeably as a mapping collar) 418.

The non-traumatic conductive surface 418 is advantageously used to make electrical measurements that indicate the location of the His bundle without having to anchor the His bundle tip electrode 16 into the endocardial tissue. The non-traumatic conductive surface 418 and the His bundle tip electrode 16 are electrically coupled within the lead body of the His bundle lead 21 and together form one conductive element for the purposes of sensing, stimulation, and impedance measurements. Drugs, for example an acute antiarrhythmic drug such as lidocaine and/or an anti-inflammatory agent such as dexamethazone sodium phosphate, can be stored, for example, within a reservoir (not shown) at the base of the His bundle tip electrode 16 for local dispensation.

The His bundle lead 21 is also provided with a His ring electrode 19. The His ring electrode 19 is preferably spaced between approximately 2 mm and 30 mm, but preferably 10 mm, from the His tip electrode 16. The His ring electrode 19 may function as the return electrode during bipolar sensing, stimulation or impedance measurement operations.

The His tip electrode 16 and the His ring electrode 19 are each connected to flexible conductors 64, 66, respectively, which may run the entire length of the His bundle lead 21. The flexible conductor 64 is connected to the His tip electrode 16 and is electrically insulated from the flexible conductor 66 by a layer of insulation. The conductor 66 is connected to the His ring electrode 19. The flexible conductors 64, 66 serve to electrically couple the His ring electrode 19 and the His tip electrode 16 to the His ring electrode terminal 61 and the His tip electrode terminal 50, respectively. One embodiment of the His bundle lead 21 is available from St. Jude Medical CRMD as lead model No. 1488T.

Figure 5:
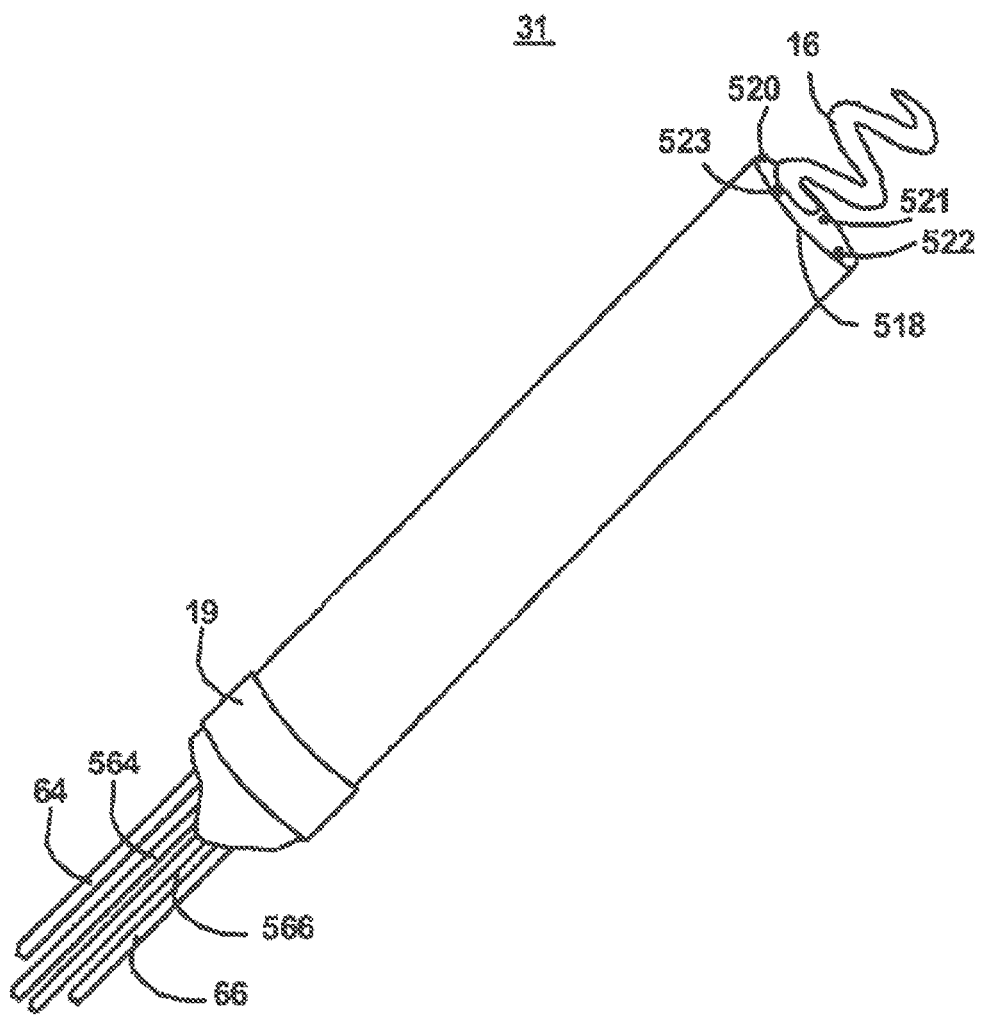
FIG. 5 is a partly fragmentary illustration of the distal end of another His bundle lead for use with the stimulation system of FIG. 3, depicting a tip electrode with an active fixation device and a non-traumatic conductive surface, a ring electrode, and four conductive sensing electrodes.

FIG. 5 illustrates an alternative His lead 31 that is generally similar in function and design to the His lead 21 shown in FIG. 4. The His lead 31 is provided with a His tip electrode 16 that includes multiple, round, closely-spaced conductive surfaces 520-523 that are arranged on a distal face 518 of the lead 31, directly facing the His bundle tissue. Though four round conductive surfaces 520-523 are shown as being uniformly distributed around the His tip electrode 16 and are electrically separated from each other by insulating material, it should be clear that a different number of conductive surfaces may alternatively be selected.

In one embodiment, a conductive surface, e.g. 520 is connected to a flexible conductor, e.g. 564 that extends along the length of the His bundle lead 31. The remaining conductive surfaces 521-523 are electrically connected together and are also connected to a flexible conductor 566 that extends along the length of the His bundle lead 31. The flexible conductors, e.g. 564, 566 are insulated from each other.

In the embodiment of FIG. 5 and with reference to FIG. 3, the device 10 includes two separate connection terminals, one for each of the two flexible conductors 564, 566 that are further connected to switch 74. The two flexible conductors 564, 566 can then be selectively connected as desired to the His sensing circuit 83, ventricular pulse generator 72, or impedance measuring circuit 112 for sensing, stimulating, and measuring tissue impedance at the site of the His bundle.

Using the lead 31, it is possible to effect stimulation with the His tip electrode 16 and the His ring electrode 19, and to effect sensing with the conductive surfaces 520-523. According to another design, the sensing is effected by the conductive surfaces 520-523 and stimulation is effected by means of the leads other than the His lead 31, for example the right atrial lead 20. For more details regarding a heart electrode equipped with multiple conductive surfaces, reference is made to U.S. Pat. Nos. 5,306,292 and 5,645,580, which are incorporated herein by reference.

During the implantation procedure, the His bundle lead 21 of FIG. 4 (or the His bundle lead 31 of FIG. 5) is introduced transvenously into the right atrium, it is then gradually advanced with the His tip electrode 16 in contact with the endocardial tissue. Electrical measurements may be made continuously as the His tip electrode 16 is advanced to determine the location of the His bundle. The non-traumatic conductive surface 418 advantageously provides electrical contact with the endocardial tissue thereby allowing electrical measurements to be performed without having to fix the His tip electrode 16 into the endocardial tissue using the His bundle tip electrode 16.

In one embodiment, tissue impedance measurements are made in order to locate the His bundle. To do so, an excitation current is applied through the His tip electrode 16. As illustrated in FIG. 6, the excitation current is preferably provided as a current limited high-frequency alternating current signal produced by a 30 kHz oscillator 550 passing through a current limiter 552. A voltage signal can then be measured between the His tip electrode 16 (or the non-traumatic conductive surface 418) and the His ring electrode 19 in a bipolar fashion. The voltage signal is related to the supplied current and the tissue impedance 554 associated with the tissue in contact with the His tip electrode 16. Thus, the measured voltage signal is processed by the impedance measuring circuit 112 to determine the impedance of the tissue in contact with His tip electrode 16. The impedance equals the voltage divided by the current.

Right atrial tissue impedance is expected to be approximately twice that of the His bundle. Using the foregoing measurement method, the right atrial tissue impedance is typically on the order of 1200-1500 ohms, whereas the His bundle tissue impedance is typically on the order of 600-800 ohms. Other impedance values can be obtained using different measurement techniques. Thus, as the His bundle lead 21 is advanced in the right atrium, a large decrease in measured tissue impedance 554, of approximately 50%, indicates that the His bundle tip electrode 16 is proximate the His bundle.

The His tip electrode 16 may then be secured in the His bundle thereby anchoring the His tip electrode 16 in contact with the His bundle tissue. The electrogram signal arising from the His bundle can then be received by the His sensing circuit 83. A bypass filter (not shown) that allows signals ranging from 30-200 Hz to be received may be used to block the high frequency alternating current excitation signal produced by the oscillator 550.

In systems and methods according to the present disclosure, a stimulation system, such as the stimulation system 10 of FIG. 3, is coupled to the heart by at least three leads in order to provide His bundle pacing (HBP). The first lead is generally used to sense and/or pace activity in the right atrium (RA) and, as a result, is positioned within the RA in proximity to the sinoatrial (SA) node. The second lead is positioned within the RA substantially opposite the SA node and near the atrioventricular (AV) node to sense and/or pace the His bundle. Cardiac resynchronization therapy (CRT) is further achieved using a left ventricle (LV) lead configured to provide electrical impulses to the LV and to measure electrical activity of the LV. In certain implementations, a right ventricle (RV) lead may also be disposed within the RV to sense and/or provide impulses to the RV.

Notably, the systems and methods described herein may be implemented using stimulation systems in which only atrial and ventricular leads and corresponding channels are available, i.e., stimulation systems in which a dedicated His bundle pacing channel is not present. In such implementations, the ventricular lead and its corresponding channel may instead be used for sensing and pacing of the His bundle. Accordingly, a previously implanted pacing device including a ventricular lead that was used for conventional CRT may be repurposed for HBP by relocating the ventricular lead adjacent the AV node.

As described below in more detail, stimulation systems and methods according to the present disclosure generally operate by automatically determining the delay between sensing and/or pacing events of the RA and subsequent activation of the His bundle. This intrinsic delay is then used to select an appropriate pacing delay for HBP, which corresponds to a time measured from the atrial event after which an HBP impulse is delivered by the stimulation system to the His bundle. The HBP delay is generally selected such that the intrinsic response of the His bundle is preempted.

After selection of the HBP delay, various other aspects of the operation of the stimulation system may be modified to optimize or otherwise improve the efficacy of the stimulation system for use in providing CRT with HBP. For example, the amplitude of the pacing stimuli may be adjusted to increase engagement of the His-Purkinje conduction system. The HBP delay may also be adjusted to provide the best possible hemodynamic response. In implementations in which the pacing device is a biventricular implantable cardioverter-defibrillator (ICD) or pacemaker that further includes a left ventricle (LV) lead, the additional operations may also include determining a suitable delay between stimulation of the His bundle and delivery of a pacing impulse to the LV via the LV lead.

FIG. 7 is a flow chart illustrating a method 700 for automatic programming and optimization of a stimulation system, such as the stimulation system 10 of FIGS. 2 and 3. More specifically, the method 700 is directed to programming and optimization of a stimulation system 10 for purposes of providing CRT with HBP.

At operation 702, a delay between an RA event and activation of the His bundle ($t_{AE-HS}$) is automatically determined. In implementations in which the RA of a patient is relatively healthy and functional, the RA event is generally a sensed depolarization/activation of the RA as measured using an RA sensing lead or electrode. Alternatively, the RA event may correspond to a pacing of the RA by the stimulation system. Accordingly, depending on the condition of the patient heart and/or the components of the stimulation system, $t_{AE-HS}$ may correspond to one of a time between sensing activation of the RA and sensing a corresponding activation of the His bundle or a time between pacing of the RA and sensing a corresponding activation of the His bundle.

The specific method of determining $t_{AE-HS}$ may vary depending on the configuration of the stimulation system. For example, biventricular stimulation systems may include each of a first channel for monitoring electrical activity of the RA and a second channel for monitoring electrical activity of the ventricles. More specifically, the second channel may combine electrical activity of the RV and LV (such as by the ventricular sensing circuit 84 of FIG. 3) and provide the combined signal over the ventricular channel. To facilitate identification of $t_{AE-HS}$, the His bundle lead may be electrically coupled to the stimulation system such that the ventricular channel provides a combination of electrical activity of the His bundle and the LV as opposed to a combination of the RV and the LV. By varying the sensitivity of the stimulation system to electrical activity on the ventricular channel, the stimulation system may identify the onset of His potential ahead of ventricular depolarization and, as a result, may determine $t_{AE-HS}$.

An example of the foregoing process is provided below in more detail in the context of FIG. 8. In summary, the process generally includes, modifying the sensitivity of the stimulation system for a plurality of heartbeats and, for each heartbeat, measuring the corresponding delay between an atrial event and subsequent activity measured on the ventricular channel. The minimum sensitivity at which onset of His potential is measurable is generally indicated by a relative large stepwise decrease in the observed delay between the atrial event and depolarization of the His bundle between successive sensitivity settings.

In an alternative implementation, $t_{AE-HS}$ may be determined by measuring electrical activity of the heart for a single heartbeat and then executing one or more threshold identification or similar software-based routines on data corresponding to the measured electrical activity. More specifically, the stimulation system may record cardiac electrical activity, such as in the form of an electrocardiogram, for a patient heartbeat and may analyze the corresponding data to determine the onset of His potential. For example, the stimulation system may record a single heartbeat electrocardiogram in memory or a buffer and may then execute one or more threshold detection algorithms at varying sensitivity levels to identify the onset of His potential and the corresponding delay from the atrial event (i.e., $t_{AE-HS}$).

Although the previous example relies on an electrocardiogram or similar electrical activity data of a single heartbeat, in other implementations the electrical activity data analyzed by the stimulation system may instead correspond to electrical activity data obtained from multiple heartbeats and subsequently combined. For example, electrical activity data may be collected for multiple heartbeats and combined by, among other things, one or more of averaging the electrical activity data and/or filtering out or otherwise excluding particular electrical activity data (e.g., electrical activity data that is particularly noisy or that corresponds to heartbeats in which electrocardiogram morphology is significantly different from a majority of other collected heartbeats) such that the combined electrical activity data corresponds to an average or "typical" heartbeat of the patient.

At operation 704, the HBP delay ($t_{AE-HP}$) is set in order to preempt intrinsic depolarization of the His bundle. By doing so, fusion/pseudo-fusion of the HBP impulse and the intrinsic electrical signals produced within the heart are avoided. In general, this process includes setting the delay between the atrial event and pacing of the His bundle to be less than $t_{AE-HS}$, as determined during operation 702.

As previously noted, operation 702 results in the stimulation system determining an intrinsic delay between an atrial event and depolarization/activation of the His bundle (i.e., $t_{AE-HS}$). In certain implementations, a predetermined margin (e.g., 5 ms) may be added to $t_{AE-HS}$ as determined in operation 702 to account for potential variability in the intrinsic $A_E$-$H_S$ delay. Regardless of whether such a margin is used, the stimulation system may adjust its settings to provide pacing impulses to the His bundle that preempt intrinsic activation of the His bundle. For example, in certain implementations the stimulation system automatically adjusts its internal settings to provide pacing impulses to the His bundle at some predetermined time before the intrinsic activation of the His bundle. In other words, the stimulation system may automatically configure itself to provide His bundle pacing according to the formula:

$$t_{AE-HP}=t_{AE-HS}-\Delta_1$$

where $t_{AE-HP}$ is the delay between an atrial event and pacing of the His bundle, $t_{AE-HS}$ is the intrinsic delay between an atrial event and intrinsic activation of the His bundle (which, again, may be modified by an offset to account for variability), and $\Delta_1$ is a predetermined offset by which pacing of the His bundle is to preempt intrinsic activation of the His bundle. For example, in certain implementations $\Delta_1$ may be 20 ms such that the His bundle is paced 20 ms ahead of the measured intrinsic delay between atrial events and intrinsic activation of the His bundle.

As previously noted, operation 702 may further result in the determination of a minimum sensitivity at which His bundle pacing is observable. Accordingly, in addition to setting $t_{AE-HP}$, the stimulation system may also set an initial sensitivity based on the outcome of operation 702. In certain implementations the stimulation system may automatically set its sensitivity to a predetermined proportion of the minimum sensitivity identified in operation 702. For example, the stimulation system may automatically set the sensitivity to 50% (or some other reduced percentage) of the minimum sensitivity such that the stimulation system is well below the threshold sensitivity at which detection of His activation first occurs.

As previously noted, the atrial event of operation 702 may correspond to either of sensing of intrinsic depolarization/activation of the RA or may correspond to active pacing of the RA by the stimulation system. In implementations in which the atrial event is atrial sensing, $t_{AE-HP}$ determined in operation 704 would correspond to the delay to be used between sensing of an atrial depolarization/activation and pacing of the His bundle. In such implementations, an additional operation may be undertaken to further identify the delay to be used between pacing of the RA and pacing of the His bundle ($t_{AP-HP}$). By identifying this additional delay, the stimulation system may readily adapt to continue to provide stimulation of the heart even in situations in which intrinsic RA activation is no longer detectable or the RA fails to intrinsically activate. In other words, setting a value for $t_{AP-HP}$ enables the stimulation system to readily change the atrial event upon which HBP is based.

The process of identifying $t_{AP-HP}$ may include reducing the pacing applied to the RA to a low level (e.g., to 50 pulses per minute) and performing one or more of the techniques discussed above in the context of operation 702 for determining the delay between pacing of the RA and the corresponding response of the His bundle. For example, a table of delays between RA pacing and His bundle sensing may be generated for a range of sensitivities and the minimum delay ($t_{AP-HS}$) may be identified from the table. $t_{AP-HP}$ may subsequently be set to $t_{AP-HS}$ less a predetermined time such that pacing of the His bundle preempts intrinsic His activation. Mathematically, this may be represented by the following formula:

$$t_{AP-HP}=t_{AP-HS}-\Delta_2$$

where $t_{AP-HP}$ is the delay between pacing of the RA and pacing of the His bundle. $t_{AP-HS}$ is the delay between pacing of the RA and the intrinsic response of the His bundle, and $\Delta_2$ is a predetermined time applied to ensure preemption. In one example implementation, $\Delta_2$ may be 20 ms.

In an alternative approach, $t_{AP-HP}$ may be calculated directly from the delay between sensing of RA activation/depolarization and corresponding activation of the His bundle, as determined in operation 702 (i.e., $t_{AS-HS}$). For example, in one implementation, it may be assumed that $t_{AP-HS}$ is approximately a predetermined duration (e.g., 60 ms) greater than $t_{AP-HS}$. In such implementations, $t_{AP-HP}$ may be calculated accordingly to the formula:

$$t_{AP-HP} = t_{AS-HS} + \Delta_3 - \Delta_2$$

where $t_{AP-HP}$ is the delay between pacing of the RA and pacing of the His bundle, $t_{AP-HS}$ is the delay between sensing of the RA and the intrinsic response of the His bundle, and $\Delta_3$ is the assumed difference between $t_{AP-HS}$ and $t_{AS-HS}$, and $\Delta_2$ is the predetermined time applied to ensure preemption.

In certain implementations, the process of identifying $t_{AE-HP}$ (i.e., the delay between an atrial event and His pacing) may be periodically reevaluated by the system and adjusted, if necessary. For example, such adjustments may be made in order to account for prolonging of the intrinsic conduction through the AV node or similar changes in the electrical behavior of the heart. The reevaluation of $t_{AE-HP}$ may be initiated in response to various events including, without limitation, the passing of a predetermined amount of time, the occurrence of a predetermined number of cardiac cycles, or a measured change in QRS or other heartbeat parameters.

In one example reevaluation process, $t_{AE-HP}$ may be temporarily increased by a predetermined amount (e.g., 100 ms) such that the intrinsic activity of the heart may be ascertained without disabling His pacing entirely. In other words, pacing will occur either intrinsically or artificially after an extended delay. After modifying $t_{AE-HP}$, an updated delay between the atrial event of interest and intrinsic activation of the His bundle (i.e., $t_{AE-HS}'$) may be measured. The delay between the atrial event and pacing of the His bundle may then be updated to a new value ($t_{AE-HP}'$) based on $t_{AE-HS}'$.

In implementations in which the atrial event is atrial pacing (i.e., $t_{AE-HP}' = t_{AP-HP}'$), for example, $t_{AE-HP}'$ may be determined by the following formula:

$$t_{AE-HP}' = t_{AS-HS}' - \Delta_1$$

where $t_{AE-HP}'$ is the updated delay between the atrial event/atrial pacing and pacing of the His bundle, $t_{AP-HS}'$ is the new measured delay between atrial pacing and the intrinsic response of the His bundle, and $\Delta_1$ is the predetermined time applied to ensure that the intrinsic response of the His bundle is preempted by pacing of the His bundle. In such implementations, a stored delay between atrial sensing and pacing of the His bundle ($t_{AS-HP}'$) may also be updated periodically as well. For example, when updating $t_{AE-HP}'$, $t_{AS-HP}'$ may also be calculated according to the following formula:

$$t_{AS-HP}' = t_{AE-HP}' - \Delta_3 - \Delta_1$$

where $t_{AS-HP}'$ is the updated delay between atrial sensing and pacing of the His bundle, $t_{AE-HP}'$ is the updated delay between the atrial event (i.e., atrial pacing) and pacing of the His bundle, $\Delta_3$ is an assumed/predetermined difference between $t_{AS-HP}'$ and $t_{AE-HP}'$, and $\Delta_1$ is the predetermined time applied to ensure preemption of the His bundle pacing.

In implementations in which the atrial event is atrial sensing (i.e., $t_{AE-HP}' = t_{AS-HP}'$), $t_{AE-HP}'$ may be determined by the formula:

$$t_{AE-HP}' = t_{AS-HS}' - \Delta_1$$

where $t_{AE-HP}'$ is the updated delay between the atrial event/atrial sensing and pacing of the His bundle, $t_{AP-HS}'$ is the new measured delay between atrial pacing and the intrinsic response of the His bundle, and $\Delta_1$ is the predetermined time applied to ensure that the intrinsic response of the His bundle is preempted by pacing of the His bundle. In such implementations, a stored delay between atrial pacing and pacing of the His bundle ($t_{AP-HP}'$) may also be updated periodically as well. For example, when updating $t_{AE-HP}'$, $t_{AP-HP}'$ may also be calculated according to the following formula:

$$t_{AP-HP}' = t_{AE-HP}' + \Delta_3 - \Delta_1$$

where $t_{AP-HP}'$ is the updated delay between atrial pacing and pacing of the His bundle, $t_{AE-HP}'$ is the updated delay between the atrial event (i.e., atrial sensing) and pacing of the His bundle, $\Delta_3$ is an assumed/predetermined difference between $t_{AP-HP}'$ and $t_{AE-HP}'$, and $\Delta_1$ is the predetermined time applied to ensure preemption of the His bundle pacing.

As previously noted, the His bundle pacing delay may be periodically updated in response to a measured change in heartbeat morphology or similar heartbeat-related parameters. For example, one or more beats may be recorded and analyzed to identify changes in QRS morphology. In implementations in which multiple beats are recorded, the beats may be average together or otherwise combined to generate a composite or mean heartbeat. The process of recording and analyzing beats may occur at a predetermined interval based on, among other things, a particular number of cardiac cycles (e.g., every 128 cardiac cycles) or a predetermined duration (e.g., every two minutes). Analysis of the recorded beat data may include comparison of one or more aspects of the beat morphology to, among other things, previously recorded beat data of the patient, templates based on performance of the patient's own heart, or model beat data or templates, each of which is stored in an onboard memory of the system. If an absolute or relative change is detected that exceeds a predetermined threshold, the reevaluation process discussed above may be initiated to update the corresponding His bundle pacing delays. Alternatively, it no such change is detected, the His bundle pacing delay may be left unchanged.

At operation 706, the energy of the HBP impulses is set to maximize engagement of the heart's intrinsic conduction system. When performing HBP the sequence of ventricular activation can vary with the amplitude of the applied impulse. More specifically, the impulse can result in selective His capture (in which only the His bundle is captured), non-selective His capture (in which the His bundle and some amount of surrounding myocardium is captured), myocardium-only capture, non-capture, and varying degrees of right or left fascicular block. In general, however, it is often desirable to rely on the intact portions of the heart's conduction system as much as possible when performing HBP and CRT via HBP. Accordingly, in certain implementations, stimulation systems in accordance with this disclosure may automatically determine the optimal HBP impulse energy to be applied.

The specific criteria for determining an optimal HBP impulse energy may vary across applications. For example, in a first example, the optimal HBP impulse energy may be defined as the HBP impulse energy that achieves the shortest latency of LV activation after the HBP impulse is applied. In such implementations HBP impulses may be applied using various combinations of impulse amplitudes and durations and corresponding times between application of the impulses and corresponding activation of the LV may be measured. The optimal HBP impulse energy may then be identified as the combination of impulse amplitude and duration resulting in the shortest time to LV activation. In stimulation systems that include a multipolar (e.g., a quadiropolar) LV lead, the latency may be defined as either of the time to either the first or the last electrode showing activation on the corresponding unipolar electrogram.

In a second example in which the stimulation system includes a multipolar LV lead, the optimal HBP impulse energy may be defined as the HBP impulse energy that achieves the shortest LV total activation time. In such implementations, the LV activation time may be defined as the difference between the earliest and the latest activation times as measured using the LV multipolar lead. Accordingly, the stimulation system may perform HBP using varying settings, measure the LV total activation time for each impulse, and set its HBP impulse settings to match those of the impulse resulting in the shortest LV total activation time.

In a third example, the optimal HBP impulse energy may be defined as the impulse energy resulting in cardiac activity that most closely resembles that of the intrinsic heartbeats of subjects with healthy His-Purkinje conduction systems. Such activity may be based on, without limitation, one or more of QRS duration, QRS morphology, RV and/or LV activation time relative to His activation, total LV activation time, LV activation pattern, and RV-LV activation delay. For example, intrinsic beats of a subject with a healthy His-Purkinje conduction system (which may be the patient themselves) may be used to generate templates and/or values that are stored within the stimulation system and against which electrocardiogram or similar data obtained by the stimulation system may be compared. Alternatively, such templates and/or values may be obtained from empirical or other studies of individuals with healthy His-Purkinje conduction systems and preprogrammed into the stimulation system. The stimulation system may then perform HBP using varying settings, compare measured electrical activity data to the stored template/values, and set its HBP impulse settings to those that result in the closest match between the stored template/values and the measured electrical activity data.

In a fourth example, the optimal HBP impulse energy may be defined as that which results in the shortest electrogram-based QRS duration estimate (e.g., from fiducial points on the discrimination channel of the ICD or pacemaker).

At operation 708, the HBP delay ($t_{AE-HP}$) is automatically optimized. Such optimization may be particularly useful in applications in which the AV node exhibits significant conduction delay (e.g., if the intrinsic delay between sensing in the RA and activation of the His bundle exceeds 150 ms and/or pacing of the RA and activation of the His bundle exceeds 200 ms). In certain implementations, optimization of $t_{AE-HP}$ is performed by analyzing the hemodynamic response of the patient heart in response to HBP. In general, such optimization includes progressively reducing $t_{AE-HP}$ until a maximal impedance signal is obtained during diastolic filling. Such impedance may be measured, for example, between an RA electrode and the housing of the stimulation system or between the SVC coil and the housing of the stimulation system, depending on the particular configuration of the stimulation system. Such a process of measuring impedance, determining a corresponding hemodynamic response, and adjusting HBP timing is provided in U.S. Pat. No. 9,179,846, which is incorporated herein by reference.

Finally, at operation 710, the stimulation system automatically optimizes LV pacing. In general, such optimization attempts to synchronize activation of the LV with that of the RV and can be assessed in various ways.

In one example implementation of LV pacing optimization, timing of the LV impulse is modified based on QRS duration. More specifically, LV pacing impulses are delivered with varying timing and corresponding QRS waveforms are measured, such as by far-field measurement between an RA ring electrode and the housing of the stimulation system, between an SVC coil and the housing of the stimulation system, or between an RV coil and the housing of the stimulation system. The stimulation system then determines the QRS duration for each of the LV pacing impulses and determines which timing resulted in the shortest QRS duration. The stimulation system sets its LV pacing impulse timing to that which resulted in the shortest QRS duration. In one specific example, the LV pacing impulses may be initially timed to be simultaneous with the HBP impulse and may be gradually delayed to the time of His to LV depolarization while observing the QRS duration from one of an RA-to-case far-field electrogram, an SVC-to-case electrogram, or an RV coil-to-case electrogram. Another method of LV pacing optimization is provided in FIG. 9 and discussed below in more detail.

As indicated in FIG. 7, the method 700 may be executed by the stimulation system in a continuous loop, whereby delays and other settings associated with pacing of the RA, the His bundle, the LV, or any other portion of the heart may be continuously or periodically reevaluated and updated to provide optimal stimulation of the heart.

FIG. 8 is a flow chart illustrating an example method 800 for automatically sensing and determining the delay between an atrial event and activation of the His bundle. Such a method may, for example, be implemented in operation 702 in the method 700 of FIG. 7 and the atrial event may correspond to either atrial pacing or sensing of the intrinsic depolarization of the RA. Also, to the extent the atrial event is selected as atrial pacing or sensing of the intrinsic depolarization of the RA a stimulation system in accordance with this disclosure may further include functionality to perform His bundle pacing based on the other atrial event.

With reference to FIG. 8, the method 800 Includes setting each of an initial value for the delay between the atrial event and pacing of the His bundle ($t_{AE-HP}$), and a sensitivity setting for detection of depolarization of the His bundle (operation 802). In general, the initial value of $t_{AE-HP}$ is set to avoid fusion while still ensuring that a pulse is delivered should intrinsic depolarization not occur. If the atrial event is sensing depolarization of the RA, for example, $t_{AE-HP}$ may be set to 300 ms. Alternatively, if the atrial event is pacing of the RA, $t_{AE-HP}$ may be set to 360 ms. The initial sensitivity setting may vary depending on the specific stimulation system being implemented, but may generally correspond to the minimum sensitivity (or a relatively low sensitivity) at which depolarization of the His bundle may be detected. For purposes of the following example, the sensitivity of the stimulation system implementing the method 800 is assumed to have a minimum of 2 mV and the corresponding initial setting of the stimulation system is set to 2 mV.

In stimulation systems capable of atrial pacing, initial configuration of the stimulation system may further include setting a pacing rate. Such a pacing rate may be set, for example, at a rate greater than a predetermined intrinsic heart rate to avoid fusion. In one example implementation, a pacing rate of 50 pulses per minute may be used as an initial pacing setting.

In certain implementations, the channel of the stimulation system used to measure depolarization of the His bundle may be configured to be refractory for a predetermined period of time following detection of the atrial event. By doing so, electrical activity resulting from the atrial event will not be improperly read by the stimulation system as depolarization of the His bundle. For example, the His bundle channel may be refractory for 80 ms following atrial sensing and/or 130 ms following atrial pacing. In certain implementations, if electrical activity is detected during this interval, such activity may be identified as premature ventricular contraction (PVC) or atrial sensing and committed ventricular pacing may be initiated 100 ms after the atrial event.

The foregoing process of setting the initial settings of the stimulation system may be performed automatically by the stimulation system, in conjunction with a programmer/operator tasked with monitoring and configuring the stimulation system, or a combination thereof.

After establishing the initial settings of the stimulation system, the method 800 measures the delay between the atrial event and depolarization of the His bundle ($t_{AE-HS}$) (operation 804). The measured value of $t_{AE-HS}$ is then stored (operation 806) and a check is performed to determine whether the current sensitivity setting is the maximum sensitivity (or some predetermined upper sensitivity limit) (operation 808). If the current sensitivity setting is not the maximum, the sensitivity is increased (operation 810) and the process of measuring $t_{AE-HS}$ and storing the measured value is repeated until the maximum sensitivity is reached.

In the example implementation, measurements of $t_{AE-HS}$ are obtained at the initial 2 mV value and then for subsequent sensitivity settings at 0.2 mV increments. An example list of such values is provided in Table 1.

TABLE 1

| Sensitivity (mV) | $t_{AE-HS}$ (ms) |
| --- | --- |
| 2.0 | 200 |
| 1.8 | 195 |
| 1.6 | 192 |
| 1.4 | 190 |
| 1.2 | 189 |
| 1.0 | 188 |
| 0.8 | 130 |
| 0.6 | 129 |
| 0.4 | 128 |
| 0.2 | 128 |

Notably, while the previous discussion assumed that the table of values was generated by measuring $t_{AE-HS}$ for successive heart beats, in certain implementations, the different values for $t_{AE-HS}$ may instead be determined by analyzing a single heart beat (or amalgamation of multiple heart beats) using different sensitivity settings through software stored in a memory of the stimulation system.

After the minimum sensitivity is reached (0.2 mV in the example), the threshold sensitivity and corresponding $t_{AE-HS}$ may be identified (operation 812). In certain implementations, identification of the sensitivity and $t_{AE-HS}$ value may include identifying a step increase in $t_{AE-HS}$ between consecutive sensitivity settings. In the example data, for instance, such a step occurs between the 1.0 mV setting ($t_{AE-HS}$–188 ms) and the 0.8 mV setting ($t_{AE-HS}$–180 ms). Accordingly, based on such data, the threshold sensitivity may be identified as 0.8 mV and the corresponding $t_{AE-HS}$ delay (i.e., the intrinsic delay between the atrial event and depolarization of the His bundle) may be identified as 130 ms. This data may then be used to further optimize His bundle pacing by the stimulation system, as previously described in the context of FIG. 7.

FIG. 9 is a flow chart illustrating an example method 900 for automatically determining the delay to be used between pacing of the His bundle and subsequent pacing of the LV ($t_{HP-LVP}$). Such a method may be used, for example, in operation 708 of the method 700 of FIG. 7.

At operation 902, each of the delay between His bundle pacing and depolarization of the LV ($t_{HP-LVS}$), the delay between His bundle pacing and depolarization of the RV ($t_{HP-RVS}$), and the delay between pacing of the LV and depolarization of the RV ($t_{LVP-RVS}$) may be measured.

At operation 904, the stimulation system checks whether $t_{HP-RVS}$ is less than $t_{HP-LVS}$. Regardless of the outcome of this comparison, the delay between pacing of the His bundle and pacing of the LV is set to the intrinsic delay from pacing of the His bundle to depolarization of the LV less a calculated offset. However, the outcome of operation 904 will dictate how the offset is calculated.

Operation 906, for example, corresponds to instances when $t_{HP-RVS}$ is less than $t_{HP-LVS}$. In such cases, $t_{HP-LVP}$ may be calculated and set according to the following mathematical formula:

$$t_{HP-LVP} = t_{HP-LVS} - \mathrm{MIN}[t_{LVP-RVS}, 0.5^*(t_{LVP-RVS} + (t_{HP-LVS} - t_{HP-RVS}))]$$

where $t_{HP-LVP}$ is the delay between pacing of the His bundle and pacing of the LV, $t_{HP-LVS}$ is the delay between pacing of the His bundle and intrinsic depolarization of the LV, $t_{LVP-RVS}$ is the delay between pacing of the LV and intrinsic depolarization of the RV, and $t_{HP-RVS}$ is the delay between pacing of the His bundle and intrinsic depolarization of the RV. In general, by selecting the lesser of the two values for the offset, a greater amount of fusion is achieved, thereby resulting in conduction that more closely approximates intrinsic conduction of the heart.

If, on the other hand, $t_{HP-RVS}$ is greater than or equal to $t_{HP-LVS}$, operation 908 may be executed. In operation 908, $t_{HP-LVP}$ is instead set according to the following mathematical formula:

$$t_{HP-LVP} = t_{HP-LVS} - 0.5^* t_{LVP-RVS}$$

where $t_{HP-LVP}$ is the delay between pacing of the His bundle and pacing of the LV, $t_{HP-LVS}$ is the delay between pacing of the His bundle and intrinsic depolarization of the LV, and $t_{LVP-RVS}$ is the delay between pacing of the LV and intrinsic depolarization of the RV.

In an example implementation of the method 900 of FIG. 9, suppose that the values listed in Table 2 were obtained during operation 902.

TABLE 2

| | Delay (ms) |
| --- | --- |
| $t_{HP-LVS}$ | 120 |
| $t_{HP-RVS}$ | 80 |
| $t_{LVP-RVS}$ | 90 |

Applying the method 900, $t_{HP-RVS}$ is less than $t_{HP-LVS}$ (operation 904) and, as a result, the offset calculation to be used is that of operation 906. Applying the formula of operation 906, the value of $0.5^*(t_{LVP-RVS} + (t_{HP-LVS} - t_{HP-RVS})) = 65$ ms is less than $t_{LVP-RVS} = 90$ ms and, as a result, the offset to be used is 65 ms. $t_{HP-LVP}$ is then set to $t_{HP-LVS} - 0.5^*(t_{LVP-RVS} + (t_{HP-LVS} - t_{HP-RVS})) = 120$ ms–65 ms=55 ms.

The foregoing merely illustrates the principles of the present disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A method of performing cardio resynchronization therapy (CRT) on a patient heart using an implantable stimulation system, the stimulation system having at least one processor, at least one memory, a pulse generator, a stimulating electrode adapted to be disposed in proximity to a His bundle of the patient heart, and an implantable sensing electrode adapted to be implanted proximate to the left ventricle (LV) of the patient heart and adapted to sense electrical activity of the LV, the method comprising:
applying, using the pulse generator and through the stimulating electrode, a His bundle pacing (HBP) impulse having a first impulse energy;
measuring, using the implantable sensing electrode, an LV activation time in response to the HBP impulse; and
automatically modifying, based on the LV activation time, at least one setting of the pulse generator stored in the at least one memory such that a subsequent HBP impulse to be provided by the pulse generator via the stimulating electrode has a second impulse energy different from the first impulse energy.

2. The method of claim 1, wherein the at least one setting of the pulse generator includes at least one of an HBP impulse amplitude and an HBP impulse duration.

3. The method of claim 1, wherein the stimulation system further includes a second implantable sensing electrode adapted to sense electrical activity of the His bundle, the method further comprising:
identifying an atrial event, the atrial event being one of a pacing of the right atrium (RA) and a sensing of intrinsic RA activation;
identifying, using the second implantable sensing electrode, an intrinsic His bundle activation corresponding to the atrial event;
determining a His bundle activation time, the His bundle activation time being a time between the atrial event and the intrinsic His bundle activation; and
automatically setting an HBP impulse timing of the pulse generator to be less than the His bundle activation time such that HBP impulses applied using the stimulating electrode preempt intrinsic His bundle activation.

4. The method of claim 3, further comprising:
collecting dynamic impedance data corresponding to one or more cardiac functions in response to HBP impulses applied by the pulse generator; and
modifying the HBP impulse timing to maximize dynamic impedance with respect to the HBP impulses applied by the pulse generator.

5. The method of claim 1 further comprising applying, using the pulse generator, an LV impulse to the LV after an LV pacing delay ($t_{HP-LVP}$), $t_{HP-LVP}$ corresponding to a time from application of the HBP impulse after which a pacing impulse is applied to the LV.

6. The method of claim 5, wherein $t_{HP-LVP}$ results in a shortest QRS duration.

7. The method of claim 6, further comprising:
applying a plurality of LV timing impulses, each of the plurality of LV timing impulses being applied using a respective LV pacing delay;
for each LV timing impulse of the plurality of LV timing impulses, measuring a QRS waveform generated in response to application of the LV timing impulse;
for each QRS waveform, determining a respective QRS duration;
identifying a shortest QRS duration of the respective QRS durations; and
modifying an LV pacing delay setting of the pulse generator such that $t_{HP-LVP}$ equals the respective LV pacing delay of the LV timing impulse having the shortest QRS duration.

8. The method of claim 5, wherein $t_{HP-LVP}$ is based on each of a first intrinsic delay ($t_{HP-RVS}$) between HBP and a response of a right ventricle (RV) of the patient heart, a second intrinsic delay ($t_{HP-LVS}$) between HBP and a response of the LV, and a third intrinsic delay ($t_{LVP-RVS}$) between pacing of the LV and a response of the RV.

9. The method of claim 8, further comprising:
performing HBP by applying a first impulse to the His bundle;
measuring each of $t_{HP-LVS}$ and $t_{HP-RVS}$ in response to applying the first impulse;
applying a second impulse to the LV; and
measuring $t_{LVP-RVS}$ in response to applying the second impulse.

10. The method of claim 8 further comprising:
determining $t_{HP-LVS}$ is less than $t_{HP-RVS}$; and
setting $t_{HP-LVP}$ to the lesser of $t_{LVP-RVS}$ and $0.5*(t_{LVP-RVS}+(t_{HP-LVS}-t_{HP-RVS}))$.

11. The method of claim 8 further comprising:
determining $t_{HP-LVS}$ is one of greater than or equal to $t_{HP-RVS}$; and
setting $t_{HP-LVP}$ equal to $0.5*(t_{LVP-RVS})$.

12. The method of claim 5, wherein the stimulation system includes a multipolar LV lead including a plurality of LV sensing electrodes, the method further comprising:
measuring a plurality of LV activation delays, each of the plurality of LV activation delay measured using a respective LV sensing electrode of the plurality of LV sensing electrodes; and
calculating a total LV activation time by subtracting a minimum LV activation delay of the plurality of LV activation delays from a maximum LV activation delay of the plurality of LV activation delays.

13. The method of claim 12 further comprising applying, in response to determining the total LV activation time is below a total LV activation time threshold, at least one second LV impulse to the LV.

14. The method of claim 13, wherein the total LV activation time threshold is equal to one half of the minimum LV activation delay.

15. A cardiac stimulation system adapted to provide cardiac resynchronization therapy (CRT) for a patient heart, the stimulation system comprising:
a pulse generator;
a stimulating electrode coupled to the pulse generator and configured to be disposed in proximity to a His bundle of the patient heart;
an implantable sensing electrode coupled to the pulse generator, adapted to be implanted proximate to the left ventricle (LV) of the patient heart, and adapted to sense electrical activity of the LV of the patient heart;
a processor communicatively coupled to the pulse generator; and a memory communicatively coupled to the processor, the memory including instructions executable by the processor that, when executed by the processor, cause the processor to:
apply, using the pulse generator and through the stimulating electrode, a His bundle pacing (HBP) impulse having a first impulse energy;
measure, using the implantable sensing electrode, an LV activation time in response to the HBP impulse; and
automatically modify, based on the LV activation time, at least one setting of the pulse generator stored in the at least one memory such that a subsequent HBP impulse to be provided by the pulse generator via the stimulating electrode has a second impulse energy different from the first impulse energy.

16. The cardiac stimulation system of claim 15 further comprising a second implantable sensing electrode communicatively coupled to the processor and adapted to sense electrical activity of the His bundle, wherein the instructions further cause the processor to:
identify an atrial event, the atrial event being one of a pacing of the right atrium (RA) and a sensing of intrinsic RA activation;
identify, using the second implantable sensing electrode, an intrinsic His bundle activation corresponding to the atrial event;
determine a His bundle activation time, the His bundle activation time being a time between the atrial event and the intrinsic His bundle activation; and
automatically set an HBP impulse timing of the pulse generator to be less than the His bundle activation time such that HBP impulses applied using the stimulating electrode preempt intrinsic His bundle activation.

17. The cardiac stimulation system of claim 15, wherein the instructions further cause the processor to:

measure at least one hemodynamic response of the patient heart in response to application of HBP impulses; and
adjust an HBP impulse timing setting of the pulse generator to maximize a hemodynamic response corresponding to a subsequently applied impulse.

18. The cardiac stimulation system of claim 15 further comprising a left ventricle (LV) electrode coupled to the pulse generator and adapted to provide an LV impulse to the LV after an LV pacing delay ($t_{HP-LVP}$), $t_{HP-LVP}$ corresponding to a time from application of the HBP impulse.

19. The cardiac stimulation system of claim 18 wherein the instructions further cause the processor to:
apply a plurality of LV timing impulses, each of the plurality of LV timing impulses being applied using a respective LV pacing delay;
for each LV timing impulse of the plurality of LV timing impulses, measure a QRS waveform generated in response to application of the LV timing impulse;
for each QRS waveform, determine a respective QRS duration;
identify a shortest QRS duration of the respective QRS durations; and
modify an LV pacing delay setting of the pulse generator such that $t_{HP-LVP}$ equals the respective LV pacing delay of the LV timing impulse having the shortest QRS duration.

20. The cardiac stimulation system of claim 18, wherein the instructions further cause the processor to:
measure each of a first intrinsic delay ($t_{HP-RVS}$) between HBP and a response of a right ventricle (RV) of the patient heart, a second intrinsic delay ($t_{HP-LVS}$) between HBP and a response of the LV, and a third intrinsic delay ($t_{LVP-RVS}$) between pacing of the LV and a response of the RV; and
set $t_{HP-LVP}$ based on each of $t_{HP-VSR}$, $t_{HP-LVS}$, and $t_{LVP-RVS}$.

* * * * *